US011763502B2

(12) United States Patent
Dawant et al.

(10) Patent No.: US 11,763,502 B2
(45) Date of Patent: Sep. 19, 2023

(54) DEEP-LEARNING-BASED METHOD FOR METAL REDUCTION IN CT IMAGES AND APPLICATIONS OF SAME

(71) Applicant: Vanderbilt University, Nashville, TN (US)

(72) Inventors: Benoit M. Dawant, Nashville, TN (US); Jianing Wang, Nashville, TN (US); Jack H. Noble, Nashville, TN (US); Robert F. Labadie, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 297 days.

(21) Appl. No.: 17/266,180

(22) PCT Filed: Aug. 6, 2019

(86) PCT No.: PCT/US2019/045221
§ 371 (c)(1),
(2) Date: Feb. 5, 2021

(87) PCT Pub. No.: WO2020/033355
PCT Pub. Date: Feb. 13, 2020

(65) Prior Publication Data
US 2022/0084264 A1 Mar. 17, 2022

Related U.S. Application Data

(60) Provisional application No. 62/714,831, filed on Aug. 6, 2018.

(51) Int. Cl.
*G06T 11/00* (2006.01)
*G06V 10/25* (2022.01)
(Continued)

(52) U.S. Cl.
CPC ............ *G06T 11/008* (2013.01); *G06N 3/045* (2023.01); *G06T 3/0075* (2013.01);
(Continued)

(58) Field of Classification Search
CPC ... G06T 11/008; G06T 3/0075; G06T 7/0012; G06T 2207/10081; G06T 2207/20081;
(Continued)

(56) References Cited

U.S. PATENT DOCUMENTS 6,721,387 B1 * 4/2004 Naidu .................. A61B 6/5258
378/4
2011/0038516 A1 * 2/2011 Koehler .................. G06T 7/149
382/128

(Continued)

FOREIGN PATENT DOCUMENTS

CN 107481297 A 12/2017
WO 2017223560 A1 12/2017

OTHER PUBLICATIONS

EPO, "Supplementary European Search Report for EP Application No. 19846049.5", Munich, Germany, dated Mar. 28, 2022.
(Continued)

*Primary Examiner* — Van D Huynh
(74) *Attorney, Agent, or Firm* — Locke Lord LLP; Tim Tingkang Xia, Esq.

(57) ABSTRACT

A deep-learning-based method for metal artifact reduction in CT images includes providing a dataset and a cGAN. The dataset includes CT image pairs, randomly partitioned into a training set, a validation set, and a testing set. Each Pre-CT and Post-CT image pairs is respectively acquired in a region before and after an implant is implanted. The Pre-CT and Post-CT images of each pair are artifact-free CT and artifact-affected CT images, respectively. The cGAN is conditioned on the Post-CT images, includes a generator and a discrimi-
(Continued)

nator that operably compete with each other, and is characterized with a training objective that is a sum of an adversarial loss and a reconstruction loss. The method also includes training the cGAN with the dataset; inputting the post-operatively acquired CT image to the trained cGAN; and generating an artifact-corrected image by the trained cGAN, where metal artifacts are removed in the artifact-corrected image.

24 Claims, 10 Drawing Sheets

(51) Int. Cl.
  *G06T 3/00* (2006.01)
  *G06T 7/00* (2017.01)
  *G06N 3/045* (2023.01)
(52) U.S. Cl.
  CPC ............ *G06T 7/0012* (2013.01); *G06V 10/25* (2022.01); *G06T 2207/10081* (2013.01); *G06T 2207/20081* (2013.01); *G06T 2207/20084* (2013.01); *G06T 2207/30052* (2013.01)
(58) Field of Classification Search
  CPC ........... G06T 2207/20084; G06T 2207/30052; G06N 3/045; G06V 10/25; A61B 6/032; A61B 6/5252; A61B 6/5258
  USPC .......................................................... 382/131
  See application file for complete search history.

(56) References Cited

U.S. PATENT DOCUMENTS

| | | | | |
|---|---|---|---|---|
| 2011/0081071 | A1* | 4/2011 | Benson | A61B 6/5258 382/154 |
| 2013/0039556 | A1* | 2/2013 | Kachelriess | G06T 11/008 382/131 |
| 2015/0029178 | A1* | 1/2015 | Claus | A61B 6/032 345/419 |
| 2016/0078647 | A1* | 3/2016 | Schildkraut | G06T 11/005 382/131 |
| 2016/0117850 | A1* | 4/2016 | Jin | A61B 6/5258 382/131 |
| 2016/0324499 | A1* | 11/2016 | Sen Sharma | A61B 6/5258 |
| 2016/0371862 | A1* | 12/2016 | Silver | A61B 6/504 |
| 2017/0150937 | A1* | 6/2017 | Stille | G06T 11/005 |
| 2017/0177967 | A1 | 6/2017 | Reda et al. | |
| 2017/0270687 | A1* | 9/2017 | Manhart | G06T 7/11 |
| 2019/0104940 | A1* | 4/2019 | Zhou | A61B 5/0035 |
| 2019/0164288 | A1* | 5/2019 | Wang | G06T 5/005 |
| 2019/0333219 | A1* | 10/2019 | Xu | G06T 11/008 |
| 2021/0000438 | A1* | 1/2021 | Wang | G06T 11/008 |
| 2021/0110584 | A1* | 4/2021 | Claessen | G06T 7/0012 |

OTHER PUBLICATIONS

Wang Jianing et al: "Conditional Generative Adversarial Networks for Metal Artifact Reduction in CT Images of the Ear", 2018.
Yi Xin et al: "Sharpness-Aware Low-Dose CT Denoising Using Conditional Generative Adversarial Network", 2018.
Ghani Murammad Usman et al: "Deep Learning-Based Sinogram Completion for Low-Dose CT", 2018 IEEE.
Korean Intellectual Property Office (ISR/KR), "International Search Report for PCT/US2019/045221", Korea, dated Dec. 5, 2019.
Park, H.S. et al., "Machine-learning-based nonlinear decomposition of CT images for metal artifact reduction", arXiv: 1708.00244v1 [physics.med-ph], 2017, pp. 1-8, Seoul, South Korea.
Gjesteby, L et al., "Deep learning methods to guide CT image reconstruction and reduce metal artifacts", Medical maging, Proc. of SPIE, Feb. 11-16, 2017, vol. 10132, Article No. 101322W-1, pp. 1-7.
National Institute on Deafness and Other Communication Disorders, 2011, NIDCD Fact Sheet: Cochlear Implants, NIH Publication No. 11-4798 National Institutes of Health, Bethesda, MD, USA.
L. Gjesteby, B. De Man, Y. Jin, H. Paganetti, J. Verburg, D. Giantsoudi, and G. Wang, Metal artifact reduction in CT: where are we after four decades? IEEE Access, 4 (2016), pp. 5826-5849 doi: 10.1109/Access.2016.2608621.
L. Gjesteby, Q. Yang, Y. Xi, B. Claus, Y. Jin, B. De Man, and G. Wang, Reducing metal streak artifacts in CT images via deep learning: pilot results. 14th Int. Meet. Fully Three-Dimensional Image Reconstr. Radiol. Nucl. Med., 14 (6) (2017), pp. 611-614. doi: 10.12059/Fully3D.2017-11-3202009.
I. J. Goodfellow, J. Pouget-Abadie, M. Mirza, B. Xu, D. Warde-Farley, S. Ozair, A. Courville, and Y. Bengio, Generative adversarial nets. In NIPS 2014. URL: http://papers.nips.cc/paper/5423-generative-adversarial-nets.pdf.
K. He, X. Zhang, S. Ren, and J. Sun, Deep residual learning for image recognition. In CVPR 2016. doi: 10.1109/CVPR.2016.90.
S. Holm, A simple sequentially rejective multiple test procedure. Scandinavian Journal of Statistics. 6 (2) (1979), pp. 65-70. doi: 10.2307/4615733.
P. Isola, J. Zhu, T. Zhou, and A. A. Efros, Image-to-image translation with conditional adversarial networks. In CVPR 2017. doi: arXiv:1611.07004.
D. P. Kingma and J. Ba, Adam: a method for stochastic optimization. In ICLR 2015. doi: arXiv:1412.6980.
F. Maes, A. Collignon, D. Vandermeulen, G. Marchal, and P. Suetens, Multimodality image registration by maximization of mutual information IEEE Trans Med. Imaging, 16 (2) (1997), pp. 187-198. doi: 10.1109/42.563664.
J. H. McDonald. 2014. Handbook of Biological Statistics (3rd ed.). Sparky House Publishing, Baltimore, Maryland.
M. Mirza and S. Osindero, Conditional generative adversarial nets. arXiv:1411.1784 [cs, stat], 2014. doi: arXiv:1411.1784.
J.H. Noble, R.F. Labadie, O. Majdani, and B.M. Dawant, Automatic segmentation of intracochlear anatomy in conventional CT. IEEE Trans. Biomed. Eng., 58 (9) (2011), pp. 2625-2632. doi: 10.1109/TBME.2011.2160262.
J. H. Noble, R. F. Labadie, R. H. Gifford, and B. M. Dawant, Image-guidance enables new methods for customizing cochlear implant stimulation strategies. IEEE Trans. Neural Syst. Rehabil. Eng., 21 (5) (2013), pp. 820-829. doi: 10.1109/TNSRE.2013.2253333.
H.S. Park, S. M. Lee, H. P. Kim, and J. K. Seo, Machine-learning-based nonlinear decomposition of CT images for metal artifact reduction. arXiv:1708.00244 [physics.med ph], 2017. doi: arXiv:1708.00244.
F. A. Reda, T. R. McRackan, R. F. Labadie, B. M. Dawant, and J. H. Noble, Automatic segmentation of intra-cochlear anatomy in post-implantation CT of unilateral cochlear Implant recipients. Med. Image Anal., 18 (3) (2014), pp. 605-615. doi: 10.1016/j.media.2014.02.001.
F. A. Reda, J. H. Noble, R. F. Labadie, and B. M. Dawant, An artifact-robust, shape library-based algorithm for automatic segmentation of inner ear anatomy in post-cochlear-implantation CT. SPIE Proceedings vol. 9034, Medical Imaging 2014: Image Processing; 90342V (2014). doi: 10.1117/12.2043260.
Z. Wang, A. C. Bovik, H. R. Sheikh, and E. P. Simoncelli, Image quality assessment: from error visibility to structural similarity. IEEE Trans. Image Process , 13 (4) (2004), pp. 600-612. doi: 10.1109/TIP.2003.819861.
W. M. Wells III, P. Viola, H. Atsumi, S. Nakajima, and Ron Kikinis, Multi-modal volume registration by maximization of mutual information. Med. Image Anal., 1 (1) (1996), pp. 35-51. URL: https://doi.org/10.1016/31361-8415(01)80004-9.
X. Yi, E. Walia, and P. Babyn, Generative adversarial network in medical imaging: a review. arXiv:1809.07294 [cs.CV], 2018. doi: arXiv:1809.07294.
Y. Zhang and H. Yu, Convolutional neural network based metal artifact reduction in x-ray computed tomography. IEEE Trans. Med. Imaging, 37 (6) (2018), pp. 1370-1381. doi: 10.1109/TMI.2018.2823083.

(56) References Cited

OTHER PUBLICATIONS

Y. Zhao, B. M. Dawant, R. F. Labadie, and J. H. Noble, Automatic localization of closely-spaced cochlear implant electrode arrays in clinical CTs. Med. Phys., 45 (11) (2018), pp. 5030-5040. doi:10.1002/mp.13185.

Y. Zhao, S. Chakravorti, R. F. Labadie, B. M. Dawant, and J. H. Noble, Automatic graph-based method for localization of cochlear implant electrode arrays in clinical CT with sub-voxel accuracy. Med. Image Anal., 52 (2019), pp. 1-12. doi: 10.1016/j.media.2018.11.005.

J. Zhu, T. Park, P. Isola, and A. A. Efros, Unpaired image-to-image translation using cycle-consistent adversarial networks. In ICCV2017. doi: arXiv:1703.10593.

Reda, F. A. et al.: Automatic segmentation of intra-cochlear anatomy in post-implantation CT. Proc. SPIE 8671, Medical Imaging 2013: Image-Guided Procedures, Robotic Interventions, and Modeling, 867101 (2013).

Ronneberger, O., Fischer, P., and Brox, T.: U-Net: convolutional networks for biomedical image segmentation. arXiv: 1505.04597, (2015).

Johnson, J., Alahi, A., and Fei-Fei. L.: Perceptual losses for real-time style transfer and super-resolution. Lect. Notes Comput. Sci. (including Subser. Lect. Notes Artif. Intell. Leet. Notes Bioinformatics) 9906 LNCS, 694-711 (2016).

Li, C. and Wand, M.: Precomputed real-time texture synthesis with markovian generative adversarial networks. Lect. Notes Comput. Sci. (including Subser. Lect. Notes Artif. Intell. Lect. Notes Bioinformatics) 9907 LNCS, 702-716 (2016.).

Ledig, C. et al.: Photo-realistic single image super-resolution using a generative adversarial network. arXiv:1609.04802, (2017).

\* cited by examiner

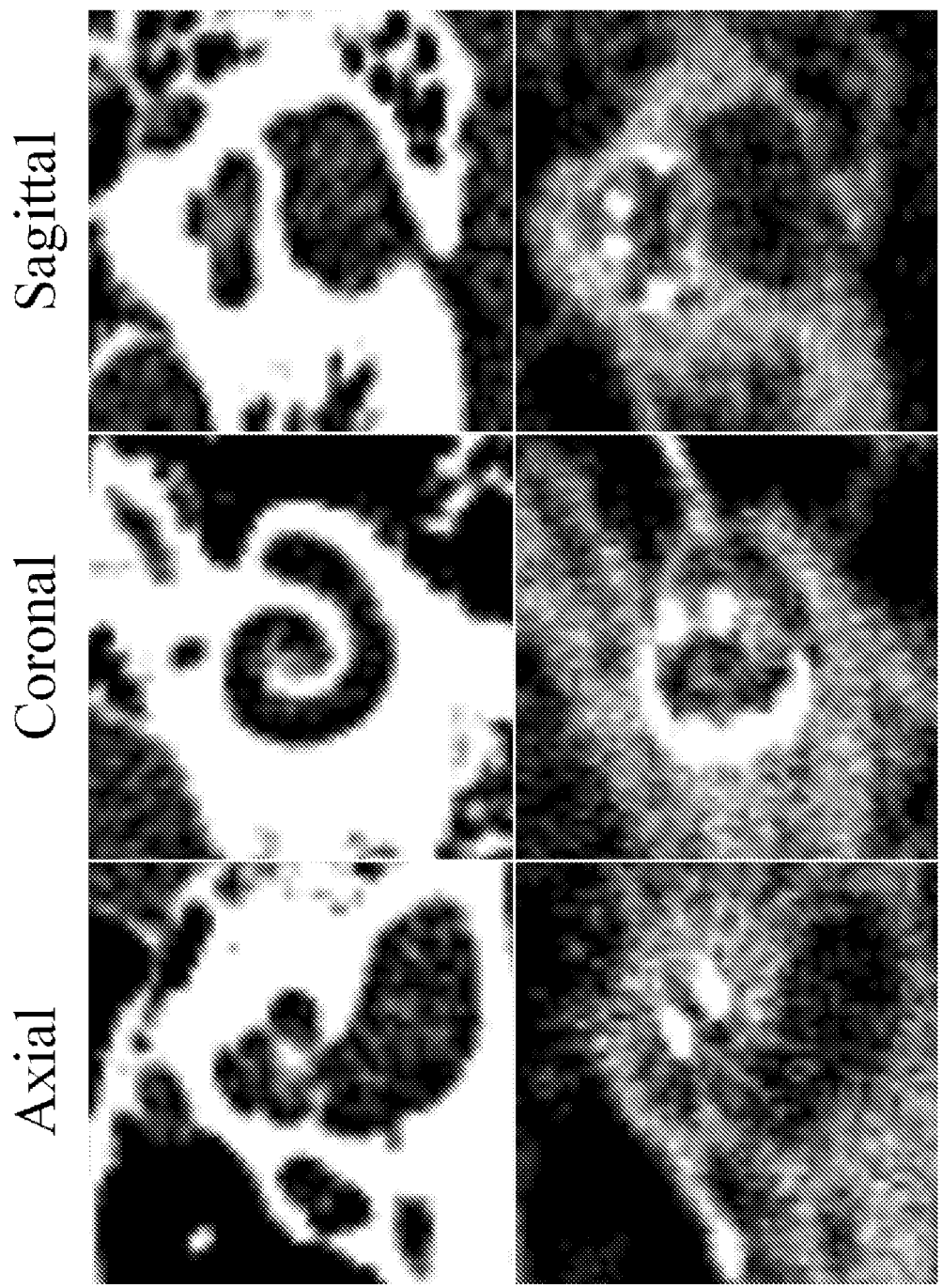

DEEP-LEARNING-BASED METHOD FOR METAL REDUCTION IN CT IMAGES AND APPLICATIONS OF SAME

CROSS-REFERENCE TO RELATED PATENT APPLICATION

This application claims priority to and the benefit of, pursuant to 35 U.S.C. § 119(e), U.S. Provisional Patent Application Ser. No. 62/714,831, filed Aug. 6, 2018, which is incorporated herein in its entirety by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [12] represents the 12th reference cited in the reference list, namely, J. H. Noble, R. F. Labadie, O. Majdani, and B. M. Dawant, Automatic segmentation of intracochlear anatomy in conventional CT. IEEE Trans. Biomed. Eng., 58 (9) (2011), pp. 2625-2632. doi: 10.1109/TBME.2011.2160262.

STATEMENT AS TO RIGHTS UNDER FEDERALLY-SPONSORED RESEARCH

The present invention was made with government support under Contract Nos. DC014037 and DC014462 awarded by the National Institutes of Health. The government has certain rights in the invention.

FIELD OF THE INVENTION

The invention relates generally to cochlear implants, and more particularly, to methods and systems for optimizing selection and placement of cochlear implant electrode arrays using patient-specific cochlear information and applications of same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

The cochlea is a component of the inner ear. It is a spiral-shaped cavity located inside the bony labyrinth that contains two main cavities: the scala vestibuli and the scala tympani. The modiolus is a porous bone around which the cochlea is wrapped that hosts the cochlear nerve and the spiral ganglions. These structures are shown in FIG. 1 and referred together as ICA (intra cochlear anatomy) structures. Cochlear implants (CIs) are surgically implanted neural prosthetic devices that are used to treat severe-to-profound hearing loss [1]. CIs bypass the normal acoustic hearing process by replacing it with direct stimulation of neural pathways using an implanted electrode array. After implantation, CIs are programmed by audiologists who adjust a processor's settings to send the appropriate signals to each of the implant's electrode. The efficacy of the CI programming is sensitive to the spatial relationship between the CI electrodes and ICA structures. Providing accurate information about the position of the contacts with respect to these structures can thus help audiologists to fine-tune and customize CI programming [13]. To provide this information we have developed a number of algorithms that permit determining the position of implanted electrodes relative to the ICA using pre- and post-implantation CTs.

Pre-implantation CT (Pre-CT) images and post-implantation CT (Post-CT) images of the ear are acquired before and after the surgery, respectively. The CI electrodes are localized in the Post-CT images using the automatic methods proposed by Zhao et al. [21, 22]. It is difficult to directly localize the ICA in the Post-CT images due to the strong artifacts produced by the metallic CI electrodes. The ICA is thus localized in the Pre-CT images and the position of the CI electrodes relative to the ICA is obtained by registering the Pre-CT images and the Post-CT images. In order to localize the ICA in the Pre-CT images, where the ICA is only partially visible, Noble et al. [12] have developed a method, which we refer to as PreCTseg for Pre-CT Segmentation. PreCTseg relies on a weighted active shape model created with high-resolution microCT scans of the cochlea acquired ex-vivo in which ICA structures are visible. The model is fitted to the partial information available in the Pre-CT images and used to estimate the position of structures not visible in these images.

This approach does not extend to CI recipients for whom a Pre-CT image is not available, which is the case for long-term recipients who were not scanned prior to surgery, for recipients for whom images cannot be retrieved, or for recipients implanted at institutions that use pre-operative MR images instead of CT images. To overcome this issue, Reda et al. [15-16] have proposed two methods to segment the ICA in Post-CT images. The first method, which we refer to as PostCTseg1 for Post-CT Segmentation unilateral, was developed for segmenting ICA structures in Post-CT images of CI recipients who have been implanted unilaterally [15]. PostCTseg1 relies on the intra-subject symmetry in cochlear anatomy across ears. It first segments the ICA of the contralateral normal ear and then maps the segmented structures to the implanted ear. The second method, which we refer to as PostCTseg2 for Post-CT Segmentation bilateral, was developed for segmenting ICA structures in Post-CT images of CI recipients who have been implanted bilaterally [16]. PostCTseg2 first identifies the labyrinth in the Post-CT image by mapping a labyrinth surface that is selected from a library of labyrinth surfaces, and then uses the localized labyrinth in the image as a landmark to segment the scala tympani, the scala vestibuli, and the modiolus with a standard shape model-based segmentation method.

But, while using these methods it was observed that they could at times lead to results that lacked accuracy compared to other components of the processing pipeline on which we rely to provide programming guidance to the audiologists. For instance, we can localize contacts in electrode arrays with an average accuracy better than 0.15 mm [21, 22] when the segmentation error of PostCTseg1 applied to the unilateral cases, which we refer to as IU for Implanted Unilaterally, included in this study is 0.26 mm. The segmentation error of PostCTseg2 applied to the bilateral cases, which we refer to as IB for Implanted Bilaterally, is larger and reaches 0.44 mm. These observations led us to explore ways to improve our segmentation accuracy.

Therefore, a heretofore unaddressed need exists in the art to address the aforementioned deficiencies and inadequacies.

SUMMARY OF THE INVENTION

One of the objectives of the invention is to eliminate metal artifacts created by cochlear implants in post-operative CT images. This is critical for the image-guided cochlear implant programming method we have developed over the last 10 years. This method requires segmenting the intracochlear anatomy and we typically do this with pre-operative images. We have also developed method for cases for which we do not have pre-operative images but they occasionally produce sub-optimal results, especially for bilateral cases. In this invention, we propose a method to generate synthetic pre-operative images from post-operative images. We can then apply the techniques we have developed for pre-operative images to these synthesized images. We show that using this technique produces results that are better than those obtained with our earlier methods. According to the invention, the methods can take as input an image with metal artifact and produce an image in which this artifact has been removed.

In one aspect, the invention relates to a deep-learning-based method for metal artifact reduction in a computed tomography (CT) image post-operatively acquired with an implant user in a region in which an implant is implanted.

In one embodiment, the method includes providing a dataset and a conditional generative adversarial network (cGAN). The dataset includes a plurality of CT image pairs, randomly partitioned into a training set, a validation set, and a testing set, wherein each CT image pair has a pre-implantation CT (Pre-CT) image and a post-implantation CT (Post-CT) image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively. The cGAN is conditioned on the Post-CT images, includes a generator and a discriminator that operably compete with each other, and is characterized with a training objective that is a sum of an adversarial loss and a reconstruction loss.

The method also includes training the cGAN with the plurality of CT image pairs, so that the cGAN learns a mapping from the artifact-affected CT images to the artifact-free CT images; inputting the post-operatively acquired CT image to the trained cGAN; and generating an artifact-corrected image from the post-operatively acquired CT image by the trained cGAN, wherein metal artifacts are removed in the artifact-corrected image.

In one embodiment, the method further comprises localizing anatomy structures of interest in the implanted region in the post-operatively acquired CT image by using the artifact-corrected image.

In one embodiment, said providing the dataset comprises registering the Pre-CT images to the Post-CT images using an intensity-based affine registration.

In one embodiment, said providing the dataset comprises cropping 3D patch pairs containing the structures of interest from the Pre-CT and Post-CT image pairs, so that paired patches contain the same structures of interest, one patch with the implant and the other without the implant.

In one embodiment, the cGAN is a 3D network, and the generator operably outputs a 1-channel 3D synthetic Pre-CT image responsive to an input of a 1-channel 3D Post-CT image.

In one embodiment, the generator comprises a network including a first number of convolutional blocks followed by a plurality of ResNet blocks, and a second number of convolutional blocks.

In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image G(x) from a Post-CT image x, wherein the artifact-free image G(x) is not be distinguishable from the real artifact-free Pre-CT image y by the discriminator, D, which is trained further to detect whether the produced artifact-free image G(x) is faked or not, wherein an output of the discriminator D is a probability of an image to be generated by the generator G rather than a true Pre-CT image.

In one embodiment, the training objective of the discriminator D is to assign a high value to the produced artifact-free image G(x) and a low value to the real artifact-free Pre-CT image y, while the training objective of the generator G is to fool the discriminator D to assign a low value to the produced artifact-free image G(x) and a high value to the real artifact-free Pre-CT image y.

In one embodiment, the training objective of the cGAN is characterized with a total loss, L, that is a sum of the adversarial loss, $L_{cGAN}(G, D)$, and the reconstruction loss, $L_{WL_1}(G)$, of the cGANs, wherein $$L = \arg\min_G \max_D L_{cGAN}(G, D) + \alpha L_{WL_1}(G), \quad (1)$$

$$L_{cGAN}(G, D) = \min_G \max_D \mathbb{E}_{x,y}[\log(D(x, y))] + \mathbb{E}_x[\log(1 - D(x, G(x)))], \quad (2)$$

$$L_{WL_1}(G) = \mathbb{E}_{x,y}[\|W \circ (y - G(x))\|_1] \quad (3)$$

wherein $\alpha$ is the weight of the WL1 term, and wherein W is the weighting matrix and $\circ$ is the element-wise multiplication operation.

In one embodiment, the weighting matrix W is calculated by creating a bounding box that encloses the structures of interest, wherein the number of voxels inside the bounding box is equal to $N_{in}$ and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, said training the cGAN comprises training the cGAN alternatively between one stochastic gradient descent step on the discriminator, and one step on the generator, using a minibatch size of 1 and the Adam solver with momentum 0.5.

In one embodiment, said training the cGAN comprises training the cGAN for N epochs in which a fixed learning rate is applied in the first N/2 epochs and a learning rate that is linearly reduced to zero in the second N/2 epochs, wherein N is the number of training epochs and selected so that the cGAN achieves the highest median mean structure similarity (MSSIM). In one embodiment, N=200, and the fixed learning rate is about 0.0002.

In one embodiment, said training the cGAN comprises applying image augmentation to the training set by rotating each image by a plurality of small random angles in the range of −10 and 10 degrees about the x-axis, y-axis, and z-axis, to create additional training images from each original image.

In one embodiment, the cGAN is a 2D network, wherein the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, a band-wise intensity normalization (BWN) is applied to the Post-CT patches that acts as a piecewise linear stretch, wherein a 2% percentile ($p_2$), a 98% percentile ($p_{98}$) and a 99.95% percentile ($p_{99.95}$) of the intensity values of each Post-CT patch are calculated, and the patch is separated into three channels, and wherein the whole patch is coped into channels 1, 2, and 3, the intensity values in channels 1, 2, and 3 are clamped to the ranges $p_2$ to $(p_2+p_{98})/2$, $(p_2+p_{98})/2$ to $p_{98}$, and $p_{98}$ to $p_{99.95}$, respectively, and each channel is normalized to the −1 to 1 range.

In one embodiment, for each Pre-CT patch, the intensity values are clamped to the range between the bottom 1% and the top 1% voxel values, and the Pre-CT patch is normalized to the −1 to 1 range.

In one embodiment, the region of interest is a region in which an implant is implanted, wherein the region of interest includes ear, brain, heart, or other organs of a living subject. In one embodiment, the structures of interest comprise anatomical structures in region of interest. In one embodiment, the anatomical structures comprise intra cochlear anatomy (ICA). In one embodiment, the implant is a cochlear implant, a deep brain stimulator, or a pacemaker.

In another aspect, the invention relates to a method for localizing structures of interest (SOI) in a computed tomography (CT) image post-operatively acquired with an implant user in a region in which an implant is implanted.

In one embodiment, the method includes inputting the post-operatively acquired CT image to a trained conditional generative adversarial network (cGAN); and generating an synthetic Pre-CT image from the post-operatively acquired CT image by the trained cGAN, wherein the synthetic Pre-CT image is an artifact-corrected image in which metal artifacts are removed; applying a segmentation algorithm designed to operate on a Pre-CT image to segment the synthetic Pre-CT image to localizing the SOI.

In one embodiment, the trained cGAN comprises a cGAN having a generator and a discriminator that operably compete with each other, being characterized with a training objective that is a sum of an adversarial loss and a reconstruction loss, and being trained with a dataset comprising a plurality of CT image pairs, randomly partitioned into a training set, a validation set, and a testing set, wherein each CT image pair has a pre-implantation CT (Pre-CT) image and a post-implantation CT (Post-CT) image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively.

In one embodiment, the cGAN is trained to learn a mapping from the artifact-affected CT images to the artifact-free CT images.

In one embodiment, the cGAN is a 3D network, wherein the generator operably outputs a 1-channel 3D synthetic Pre-CT image responsive to an input of a 1-channel 3D Post-CT image.

In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image $G(x)$ from a Post-CT image $x$, wherein the artifact-free image $G(x)$ is not be distinguishable from the real artifact-free Pre-CT image $y$ by the discriminator, D, which is trained further to detect whether the produced artifact-free image $G(x)$ is faked or not, wherein an output of the discriminator D is a probability of an image to be generated by the generator G rather than a true Pre-CT image.

In one embodiment, the training objective of the discriminator D is to assign a high value to the produced artifact-free image $G(x)$ and a low value to the real artifact-free Pre-CT image y, while the training objective of the generator G is to fool the discriminator D to assign a low value to the produced artifact-free image $G(x)$ and a high value to the real artifact-free Pre-CT image y.

In one embodiment, the training objective of the cGAN is characterized with a total loss, L, that is a sum of the adversarial loss, $L_{cGAN}(G, D)$, and the reconstruction loss, $L_{WL_1}(G)$, of the cGANs, which satisfy Eqs. (1)-(2) respectively.

In one embodiment, the weighting matrix W is calculated by creating a bounding box that encloses the structures of interest, wherein the number of voxels inside the bounding box is equal to $N_{in}$ and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, said training the cGAN comprises training the cGAN alternatively between one stochastic gradient descent step on the discriminator, and one step on the generator, using a minibatch size of 1 and the Adam solver with momentum 0.5.

In one embodiment, said training the cGAN comprises training the cGAN for N epochs in which a fixed learning rate is applied in the first N/2 epochs and a learning rate that is linearly reduced to zero in the second N/2 epochs, wherein N is the number of training epochs and selected so that the cGAN achieves the highest median mean structure similarity (MSSIM). In one embodiment, N=200, and the fixed learning rate is about 0.0002.

In one embodiment, said training the cGAN comprises applying image augmentation to the training set by rotating each image by a plurality of small random angles in the range of −10 and 10 degrees about the x-axis, y-axis, and z-axis, to create additional training images from each original image.

In one embodiment, the cGAN is a 2D network, wherein the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, the region of interest is a region in which an implant is implanted, wherein the region of interest includes ear, brain, heart, or other organs of a living subject.

In yet another aspect, the invention relates to a non-transitory tangible computer-readable medium storing instructions which, when executed by one or more processors, cause a system to perform the above disclosed methods.

In a further aspect, the invention relates to a system for metal artifact reduction in a CT image post-operatively acquired with an implant user in a region in which an implant is implanted.

In one embodiment, the system includes a dataset comprising a plurality of CT image pairs, randomly partitioned into a training set, a validation set, and a testing set, wherein each CT image pair has a Pre-CT image and a Post-CT image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively; a cGAN having a generator and a discriminator that operably compete with each other, and being characterized with a training objective that is a sum of an adversarial loss and a reconstruction loss; and a microcontroller coupled with the dataset and the cGAN and configured to train the cGAN with the training set of the plurality of CT image pairs, such that once the post-operatively acquired CT image is input into the trained cGAN, the train cGAM generates an artifact-corrected image from the post-operatively acquired CT image, wherein metal artifacts are removed in the artifact-corrected image.

In one embodiment, the microcontroller is further configured to register the Pre-CT images to the Post-CT images using an intensity-based affine registration.

In one embodiment, the microcontroller is further configured to crop 3D patch pairs containing the structures of interest from the Pre-CT and Post-CT image pairs, so that paired patches contain the same structures of interest, one patch with the implant and the other without the implant.

In one embodiment, the cGAN is a 3D network, and the generator operably outputs a 1-channel 3D synthetic Pre-CT image responsive to an input of a 1-channel 3D Post-CT image.

In one embodiment, the generator comprises a network including a first number of convolutional blocks followed by a plurality of ResNet blocks, and a second number of convolutional blocks.

In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image G(x) from a Post-CT image x, wherein the artifact-free image G(x) is not be distinguishable from the real artifact-free Pre-CT image y by the discriminator, D, which is trained further to detect whether the produced artifact-free image G(x) is faked or not, wherein an output of the discriminator D is a probability of an image to be generated by the generator G rather than a true Pre-CT image.

In one embodiment, the training objective of the discriminator D is to assign a high value to the produced artifact-free image G(x) and a low value to the real artifact-free Pre-CT image y, while the training objective of the generator G is to fool the discriminator D to assign a low value to the produced artifact-free image G(x) and a high value to the real artifact-free Pre-CT image y.

In one embodiment, the training objective of the cGAN is characterized with a total loss, L, that is a sum of the adversarial loss, $L_{cGAN}$ (G, D), and the reconstruction loss, $L_{WL_1}$(G), of the cGANs, which satisfy Eqs. (1)-(2) respectively.

In one embodiment, the weighting matrix W is calculated by creating a bounding box that encloses the structures of interest, wherein the number of voxels inside the bounding box is equal to $N_{in}$, and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, the cGAN is trained alternatively between one stochastic gradient descent step on the discriminator, and one step on the generator, using a minibatch size of 1 and the Adam solver with momentum 0.5.

In one embodiment, the cGAN is trained for N epochs in which a fixed learning rate is applied in the first N/2 epochs and a learning rate that is linearly reduced to zero in the second N/2 epochs, wherein N is the number of training epochs and selected so that the cGAN achieves the highest median MSSIM. N=200, and the fixed learning rate is about 0.0002.

In one embodiment, the microcontroller is further configured to apply image augmentation to the training set by rotating each image by a plurality of small random angles in the range of −10 and 10 degrees about the x-axis, y-axis, and z-axis, to create additional training images from each original image.

In one embodiment, the cGAN is a 2D network, and the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, the region of interest is a region in which an implant is implanted, wherein the region of interest includes ear, brain, heart, or other organs of a living subject. In one embodiment, the structures of interest comprise anatomical structures in region of interest. In one embodiment, the anatomical structures comprise ICA. In one embodiment, the implant is a cochlear implant, a deep brain stimulator, or a pacemaker.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

FIGS. 2A-2B shows three orthogonal views of the Pre-CT (FIG. 2A) and the Post-CT (FIG. 2B) of an example ear.

DETAILED DESCRIPTION OF THE INVENTION

Figure 1:
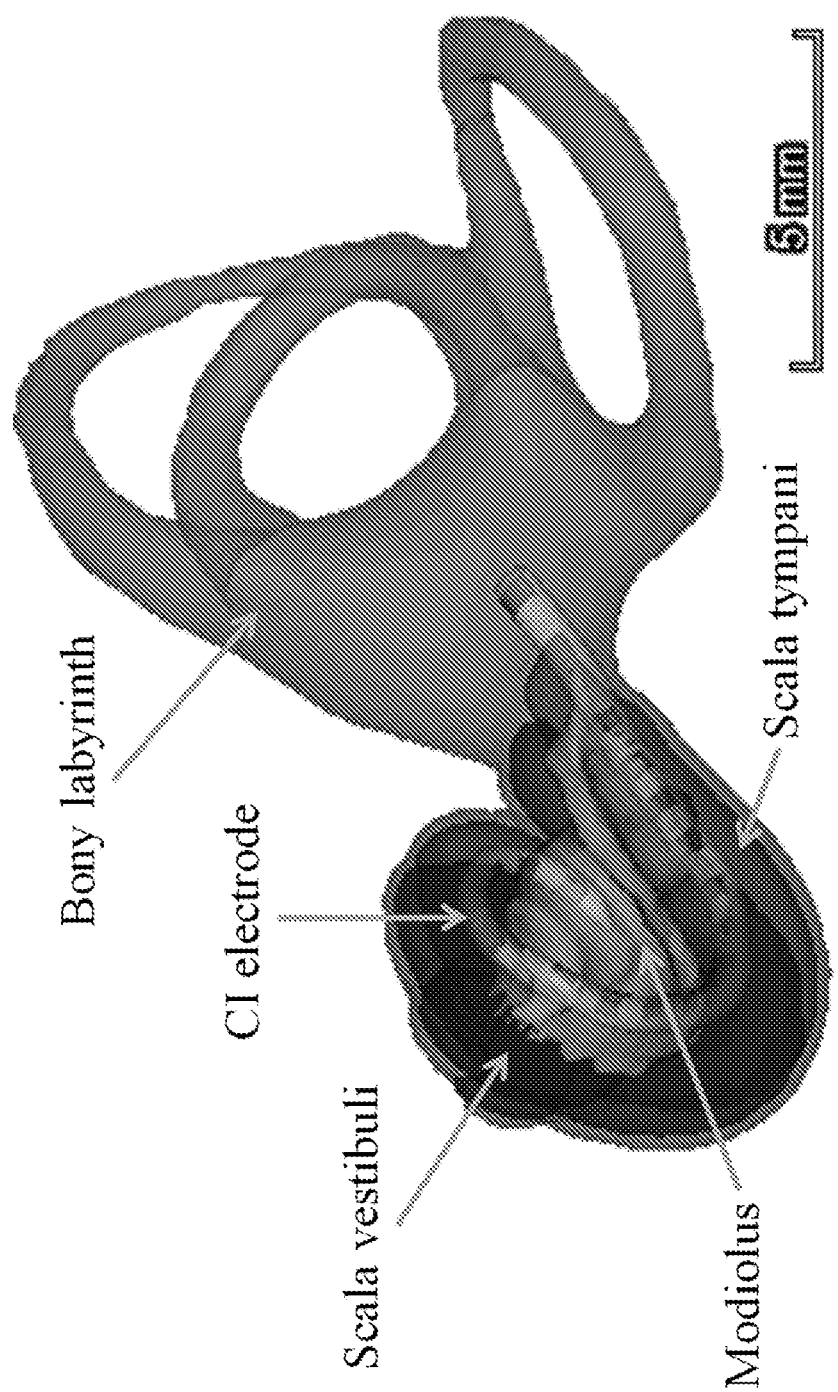
FIG. 1 shows schematically an illustration of intra cochlear anatomical structures and CI electrodes.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures. is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving", and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the term "Pre-CT" is an abbreviation of "pre-implantation computed tomography (CT)"; the term "Post-CT" is an abbreviation of "post-implantation CT"; the term "cCT" is an abbreviation of "conventional CT"; the term "lCT" is an abbreviation of "low-dose CT"; the term "GAN" is an abbreviation of "generative adversarial net"; the term "cGAN" is an abbreviation of "conditional generative adversarial network"; the term "WL1" is an abbreviation of "weighted L1"; the term "P2PE" is an abbreviation of "point-to-point error"; the term "SSIM" is an abbreviation of "structural similarity"; the term "MSSIM" is an abbreviation of "mean structure similarity"; and the term "STD" is an abbreviation of "standard deviation".

As used herein, the term "TB ears" refers to the ears of the cochlear implants recipients who have been implanted bilaterally, while the term "TU ears" refers to the ears of the cochlear implants recipients who have been implanted unilaterally.

As used herein, the term "PreCTseg" refers to a method for segmenting intra cochlear anatomy structures in pre-implantation CTs of cochlear implants recipients.

As used herein, the term "PostCTseg1" refers to a method for segmenting intra cochlear anatomy structures in post-implantation CTs of cochlear implants recipients who have been implanted unilaterally.

As used herein, the term "PostCTseg2" refers to a method for segmenting intra cochlear anatomy structures in post-implantation CTs of cochlear implants recipients who have been implanted bilaterally.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Metallic implants in the human body can cause artifacts in computed tomography (CT) scans. Methods for the metal artifact reduction (MAR) in CTs have been investigated for nearly 40 years [2]. MAR algorithms can be roughly divided into three groups: physical effects correction, interpolation in the projection domain, and iterative reconstruction [20]. Despite these efforts, developing MARs for dense metal implants and for multiple metallic objects in the field of view remains challenging and there is no known universal solution [2].

Conditional generative adversarial networks (cGANs) [7, 11] have emerged as a general-purpose solution to image-to-image translation problems. In one aspect of the invention, we disclose an approach based on cGANs for MAR. At the training phase, a cGAN learns a mapping from the artifact-affected CTs to the artifact-free CTs. At the inference phase, given an artifact-affected CT, the cGAN produces an artifact-corrected image. We apply the method to CT ear images of cochlear implants (CIs) recipients and get remarkable results.

Compared to the current leading traditional MAR methods, which generally necessitate the raw data from CT scanners [1], our approach is a post reconstruction processing method for which the raw data is not required. Our results also indicate that the post reconstruction processing methods, which have been considered to be ineffective [1], can in fact be effective. To the best of our knowledge, published MAR methods based on machine learning either depend on existing traditional MAR methods or require post-processing of the outputs produced by machine learning models [3, 14, 20]. However, the method according to the invention is unique in being able to synthesize directly an artifact-free image from an image in which artifacts are present.

In one aspect of the invention, a deep-learning-based method for metal artifact reduction in a CT image post-operatively acquired with an implant user in a region in which an implant is implanted, includes the following steps.

At first, a dataset and a cGAN are provided.

The dataset can be a database stored in a computer, a server, and/or a cloud server. The dataset can be editable, accessible and updatable. In one embodiment, the dataset has a plurality of CT image pairs, randomly partitioned into a training set, a validation set, and a testing set, wherein each CT image pair has a Pre-CT image and a Post-CT image respectively acquired in the region of interest of a respective implant recipient before and after an implant is implanted in the region of interest. The Pre-CT image and the Post-CT image of each CT image pair are an artifact-free CT image and an artifact-affected CT image, respectively.

The cGAN is conditioned on the Post-CT images, comprises a generator and a discriminator that operably compete with each other, and is characterized with a training objective that is a sum of an adversarial loss and a reconstruction loss.

Second, the cGAN is trained with the plurality of CT image pairs, so that the cGAN learns a mapping from the artifact-affected CT images to the artifact-free CT images.

Next, the post-operatively acquired CT image is input to the trained cGAN.

Then, an artifact-corrected image is generated from the post-operatively acquired CT image by the trained cGAN, wherein metal artifacts are removed in the artifact-corrected image.

In addition, the method further comprises localizing anatomy structures of interest in the implanted region in the post-operatively acquired CT image by using the artifact-corrected image.

In one embodiment, said providing the dataset comprises registering the Pre-CT images to the Post-CT images using an intensity-based affine registration.

In one embodiment, said providing the dataset comprises cropping 3D patch pairs containing the structures of interest from the Pre-CT and Post-CT image pairs, so that paired patches contain the same structures of interest, one patch with the implant and the other without the implant.

In one embodiment, the cGAN is a 3D network, and the generator operably outputs a 1-channel 3D synthetic Pre-CT image responsive to an input of a 1-channel 3D Post-CT image.

In one embodiment, the generator comprises a network including a first number of convolutional blocks followed by a plurality of ResNet blocks, and a second number of convolutional blocks. In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image G(x) from a Post-CT image x, wherein the artifact-free image G(x) is not be distinguishable from the real artifact-free Pre-CT image y by the discriminator, D, which is trained further to detect whether the produced artifact-free image G(x) is faked or not, wherein an output of the discriminator D is a probability of an image to be generated by the generator G rather than a true Pre-CT image.

In one embodiment, the training objective of the discriminator D is to assign a high value to the produced artifact-free image G(x) and a low value to the real artifact-free Pre-CT image y, while the training objective of the generator G is to fool the discriminator D to assign a low value to the produced artifact-free image G(x) and a high value to the real artifact-free Pre-CT image y.

In one embodiment, the training objective of the cGAN is characterized with a total loss, L, that is a sum of the adversarial loss, $L_{cGAN}(G, D)$, and the reconstruction loss, $L_{WL_1}(G)$, of the cGANs, wherein $$L = \arg\min_G \max_D L_{cGAN}(G, D) + \alpha L_{WL_1}(G), \quad (1)$$

$$L_{cGAN}(G, D) = \min_G \max_D \mathbb{E}_{x,y}[\log(D(x, y))] + \mathbb{E}_x[\log(1 - D(x, G(x)))], \quad (2)$$

$$L_{WL_1}(G) = \mathbb{E}_{x,y}[\|W \circ (y - G(x))\|_1] \quad (3)$$

wherein α is the weight of the WL1 term, and wherein W is the weighting matrix and ∘ is the element-wise multiplication operation.

In one embodiment, the weighting matrix W is calculated by creating a bounding box that encloses the structures of interest, wherein the number of voxels inside the bounding box is equal to $N_{in}$, and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, said training the cGAN comprises training the cGAN alternatively between one stochastic gradient descent step on the discriminator, and one step on the generator, using a minibatch size of 1 and the Adam solver with momentum 0.5.

In one embodiment, said training the cGAN comprises training the cGAN for N epochs in which a fixed learning rate is applied in the first N/2 epochs and a learning rate that is linearly reduced to zero in the second N/2 epochs, wherein N is the number of training epochs and selected so that the cGAN achieves the highest median mean structure similarity (MSSIM). In one embodiment, N=200, and the fixed learning rate is about 0.0002.

In one embodiment, said training the cGAN comprises applying image augmentation to the training set by rotating each image by a plurality of small random angles in the range of −10 and 10 degrees about the x-axis, y-axis, and z-axis, to create additional training images from each original image.

In one embodiment, the cGAN is a 2D network, and the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, a band-wise intensity normalization (BWN) is applied to the Post-CT patches that acts as a piecewise linear stretch, wherein a 2% percentile ($p_2$), a 98% percentile ($p_{98}$) and a 99.95% percentile ($p_{99.95}$) of the intensity values of each Post-CT patch are calculated, and the patch is separated into three channels, and wherein the whole patch is coped into channels 1, 2, and 3, the intensity values in channels 1, 2, and 3 are clamped to the ranges $p_2$ to $(p_2+p_{98})/2$, $(p_2+p_{98})/2$ to $p_{98}$, and $p_{98}$ to $p_{99.95}$, respectively, and each channel is normalized to the −1 to 1 range.

In one embodiment, for each Pre-CT patch, the intensity values are clamped to the range between the bottom 1% and the top 1% voxel values, and the Pre-CT patch is normalized to the −1 to 1 range.

In one embodiment, the region of interest is a region in which an implant is implanted, wherein the region of interest includes ear, brain, heart, or other organs of a living subject. In one embodiment, the structures of interest comprise anatomical structures in region of interest. In one embodiment, the anatomical structures comprise ICA. In one embodiment, the implant is a cochlear implant, a deep brain stimulator, or a pacemaker.

In another aspect of the invention, a method for localizing structures of interest (SOI) in a CT image post-operatively acquired with an implant user in a region in which an implant is implanted includes inputting the post-operatively acquired CT image to a trained conditional generative adversarial network (cGAN); and generating an synthetic Pre-CT image from the post-operatively acquired CT image by the trained cGAN, wherein the synthetic Pre-CT image is an artifact-corrected image in which metal artifacts are removed; applying a segmentation algorithm designed to operate on a Pre-CT image to segment the synthetic Pre-CT image to localizing the SOI.

In one embodiment, the trained cGAN comprises a cGAN having a generator and a discriminator that operably compete with each other, being characterized with a training objective that is a sum of an adversarial loss and a reconstruction loss, and being trained with a dataset comprising a plurality of CT image pairs, randomly partitioned into a training set, a validation set, and a testing set, wherein each CT image pair has a Pre-CT image and a Post-CT image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively.

In one embodiment, the cGAN is trained to learn a mapping from the artifact-affected CT images to the artifact-free CT images.

In one embodiment, the cGAN is a 3D network, and the generator operably outputs a 1-channel 3D synthetic Pre-CT image responsive to an input of a 1-channel 3D Post-CT image.

In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image G(x) from a Post-CT image x, wherein the artifact-free image G(x) is not be distinguishable from the real artifact-free Pre-CT image y by the discriminator, D, which is trained further to detect whether the produced artifact-free image G(x) is faked or not, wherein an output of the discriminator D is a probability of an image to be generated by the generator G rather than a true Pre-CT image.

In one embodiment, the training objective of the discriminator D is to assign a high value to the produced artifact-free image G(x) and a low value to the real artifact-free Pre-CT image y, while the training objective of the generator G is to fool the discriminator D to assign a low value to the produced artifact-free image G(x) and a high value to the real artifact-free Pre-CT image y.

In one embodiment, the training objective of the cGAN is characterized with a total loss, L, that is a sum of the adversarial loss, $L_{cGAN}$ (G, D), and the reconstruction loss, $L_{WL_1}$(G), of the cGANs, which satisfy Eqs. (1)-(3), respectively.

In one embodiment, the weighting matrix W is calculated by creating a bounding box that encloses the structures of interest, wherein the number of voxels inside the bounding box is equal to $N_{in}$ and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, said training the cGAN comprises training the cGAN alternatively between one stochastic gradient descent step on the discriminator, and one step on the generator, using a minibatch size of 1 and the Adam solver with momentum 0.5.

In one embodiment, said training the cGAN comprises training the cGAN for N epochs in which a fixed learning rate is applied in the first N/2 epochs and a learning rate that is linearly reduced to zero in the second N/2 epochs, wherein N is the number of training epochs and selected so that the cGAN achieves the highest median mean structure similarity (MSSIM). In one embodiment, N=200, and the fixed learning rate is about 0.0002.

In one embodiment, said training the cGAN comprises applying image augmentation to the training set by rotating each image by a plurality of small random angles in the range of –10 and 10 degrees about the x-axis, y-axis, and z-axis, to create additional training images from each original image.

In one embodiment, the cGAN is a 2D network, and the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, the region of interest is a region in which an implant is implanted, wherein the region of interest includes ear, brain, heart, or other organs of a living subject.

In a further aspect, the invention relates to a system for metal artifact reduction in a CT image post-operatively acquired with an implant user in a region in which an implant is implanted.

In one embodiment, the system includes a dataset comprising a plurality of CT image pairs, randomly partitioned into a training set, a validation set, and a testing set, wherein each CT image pair has a Pre-CT image and a Post-CT image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively; a cGAN having a generator and a discriminator that operably compete with each other, and being characterized with a training objective that is a sum of an adversarial loss and a reconstruction loss; and a microcontroller coupled with the dataset and the cGAN and configured to train the cGAN with the training set of the plurality of CT image pairs, such that once the post-operatively acquired CT image is input into the trained cGAN, the train cGAM generates an artifact-corrected image from the post-operatively acquired CT image, wherein metal artifacts are removed in the artifact-corrected image.

In one embodiment, the microcontroller is further configured to register the Pre-CT images to the Post-CT images using an intensity-based affine registration.

In one embodiment, the microcontroller is further configured to crop 3D patch pairs containing the structures of interest from the Pre-CT and Post-CT image pairs, so that paired patches contain the same structures of interest, one patch with the implant and the other without the implant.

In one embodiment, the cGAN is a 3D network, and the generator operably outputs a 1-channel 3D synthetic Pre-CT image responsive to an input of a 1-channel 3D Post-CT image.

In one embodiment, the generator comprises a network including a first number of convolutional blocks followed by a plurality of ResNet blocks, and a second number of convolutional blocks.

In one embodiment, the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

In one embodiment, the generator, G, is configured to produce an artifact-free image G(x) from a Post-CT image x, wherein the artifact-free image G(x) is not be distinguishable from the real artifact-free Pre-CT image y by the discriminator, D, which is trained further to detect whether the produced artifact-free image G(x) is faked or not, wherein an output of the discriminator D is a probability of an image to be generated by the generator G rather than a true Pre-CT image.

In one embodiment, the training objective of the discriminator D is to assign a high value to the produced artifact-free image G(x) and a low value to the real artifact-free Pre-CT image y, while the training objective of the generator G is to fool the discriminator D to assign a low value to the produced artifact-free image G(x) and a high value to the real artifact-free Pre-CT image y.

In one embodiment, the training objective of the cGAN is characterized with a total loss, L, that is a sum of the adversarial loss, $L_{cGAN}$ (G, D), and the reconstruction loss, $L_{WL_1}$(G), of the cGANs, which satisfy Eqs. (1)-(3), respectively.

In one embodiment, the weighting matrix W is calculated by creating a bounding box that encloses the structures of interest, wherein the number of voxels inside the bounding box is equal to $N_{in}$ and the number of voxels outside of the bounding box is equal to $N_{out}$; and assigning weights to the voxels inside and outside of the bounding box that are equal to $(N_{in}+N_{out})/N_{in}$ and 1, respectively.

In one embodiment, the cGAN is trained alternatively between one stochastic gradient descent step on the discriminator, and one step on the generator, using a minibatch size of 1 and the Adam solver with momentum 0.5.

In one embodiment, the cGAN is trained for N epochs in which a fixed learning rate is applied in the first N/2 epochs and a learning rate that is linearly reduced to zero in the second N/2 epochs, wherein N is the number of training epochs and selected so that the cGAN achieves the highest median MSSIM. N=200, and the fixed learning rate is about 0.0002.

In one embodiment, the microcontroller is further configured to apply image augmentation to the training set by rotating each image by a plurality of small random angles in the range of −10 and 10 degrees about the x-axis, y-axis, and z-axis, to create additional training images from each original image.

In one embodiment, the cGAN is a 2D network, wherein the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

In one embodiment, input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

In one embodiment, the region of interest is a region in which an implant is implanted, wherein the region of interest includes ear, brain, heart, or other organs of a living subject.

In one embodiment, the structures of interest comprise anatomical structures in region of interest. In one embodiment, the anatomical structures comprise ICA. In one embodiment, the implant is a cochlear implant, a deep brain stimulator, or a pacemaker.

It should be noted that all or a part of the steps according to the embodiments of the present invention is implemented by hardware or a program instructing relevant hardware. Yet another aspect of the invention provides a non-transitory computer readable storage medium/memory which stores computer executable instructions or program codes. The computer executable instructions or program codes enable a computer or a similar computing system to complete various operations in the above disclosed method for privilege management. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Without intent to limit the scope of the invention, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Metal Artifact Reduction for Segmentation of the Intra Cochlear Anatomy in Ct Ear Images with 2D eGAN In this first exemplary study, we disclose an approach based on a cGAN for the MAR in CT ear images of cochlear implants (CIs) recipients. First, we train the 2D cGAN to synthesize artifact-free images from the Post-CT images with an input of a 2D slice in a volume in which the artifacts are present and whose output is the corresponding synthetic artifact-free image. Once this is done for all slices, the synthetic 2D images are stacked to each other and PreCTseg method is applied to the synthetic volume. Results obtained with PreCTseg method on the synthesized volumes and the real pre-CT volumes can then be compared to assess the efficacy of the artifact removal method. Our training set contains paired pre-implantation and post-implantation CTs of 90 ears. At the training phase, the cGAN learns a mapping from the artifact-affected CTs to the artifact-free CTs. At the inference phase, given new metal-artifact-affected CTs, the cGAN produces CTs in which the artifacts are removed. As a pre-processing step, we also disclose a band-wise normalization (BWN) method, which splits a CT image into three channels according to the intensity value of each voxel and we show that this method improves the performance of the cGAN. We test the cGAN on post-implantation CTs of 74 ears and the quality of the artifact-corrected images is evaluated quantitatively by comparing the segmentations of intra-cochlear anatomical structures, which are obtained with a previously published method, in the real pre-implantation and the artifact-corrected CTs. We show that the method leads to an average surface error of 0.18 mm which is about half of what could be achieved with a previously proposed technique.

Dataset

In this exemplary study, the dataset includes Pre-CT and Post-CT pairs of 164 ears. It should be noted that Pre-CT and Post-CT pairs of other numbers of ears (or other regions of a living subject) can also be utilized to practice the invention. All these CTs have been acquired with the CIs recipients in roughly the same position. The CTs are acquired with several conventional scanners (GE BrightSpeed, LightSpeed Ultra; Siemens Sensation 16; and Philips Mx8000 IDT, iCT 128, and Brilliance 64) and a low-dose flat-panel volumetric CT scanner (Xoran Technologies xCAT® ENT). The typical voxel size is 0.25×0.25×0.3 mm$^3$ for the conventional CTs (cCTs), and 0.4×0.4×0.4 mm$^3$ for the low-dose CTs (lCTs). The 164 ears are randomly partitioned into a set of 90 for training and a set of 74 for testing. 82 of the 90 ears used for training have Post-CTs of type lCT and Pre-CTs of type cCT, and the remaining 8 ears have both Post-CTs and Pre-CTs of type cCT. 62 of the 74 ears for testing have Post-CTs of type lCT and Pre-CTs of type cCT, and the remaining 12 ears have both Post-CTs and Pre-CTs of type cCT.

cGAN

According to the invention, a conditional generative adversarial network (cGAN) framework [7] is used. Typically, generative adversarial nets (GANs) are implemented by a system of a generative network (also called as a generator) (G) and a discriminative network (also called as a discriminator) (D) that are competing with each other. G learns a mapping between a latent space and a particular data distribution of interest, while D discriminates between instances from the true data distribution and candidates produced by G. The training objective of G is to increase the error rate of D, i.e., to fool D by producing synthesized candidates that appear to come from the true data distribution [4]. The cGANs are a special case of GANs in which both G and D are conditioned on additional information that is used to direct the data generation process. This makes cGANs suitable for image-to-image translation task, where G is conditioned on an input image and generates a corresponding output image [7, 11].

For the cGAN including the generator G and the discriminator D, the total loss can be expressed as $$L = \arg\min_G \max_D L_{cGAN}(G, D) + \lambda L_{L_1}(G) \quad (1\text{-}1)$$

wherein $$L_{cGAN}(G, D) = \mathbb{E}_{x,y}[\log(D(x, y))] + \mathbb{E}_{x,z}[\log(1 - D(x, G(x, z)))] \quad (1\text{-}2)$$

is the adversarial loss and $L_{L_1}(G)$ is the L1 norm loss. G is tasked with producing an artifact-corrected image from a Post-CT x and a random noise vector z. The image generated by G should not be distinguishable from the real artifact-free Pre-CT y by D, which is trained to do as well as possible to detect G's "fakes". The generated images need to be similar to y in the L1 sense.

In certain embodiments, we explore two generator architectures: (1) a U-net (UNet) [25], and (2) a network that contains two stride-2 convolutions, 9 residual blocks, and two fractionally strided convolutions with stride ½(ResNet) [5, 23, 26-27]. For the discriminator, we use a 70×70 PatchGAN [4, 28] that aims to determine whether 70×70 overlapping image patches are real or fake. We run the PatchGAN convolutationally across the image, averaging all responses to provide the ultimate output of D.

Image Pre-Processing

The Pre-CTs are registered to the Post-CTs using intensity-based affine registration techniques. The registrations are visually inspected and confirmed to be accurate. 3D patch pairs that contain the cochlea are cropped from the Pre-CTs and Post-CTs, i.e., paired patches contain the same cochlea; one patch with and the other without the implant, as shown in FIGS. 2A (Pre-CTs) and 2B (Post-CTs). These patches are then upsampled to 0.1×0.1×0.1 mm$^3$.

We apply a band-wise intensity normalization (BWN) to the Post-CT patches that acts as a piecewise linear stretch. For each 3D patch, we calculate the 2% percentile ($p_2$), the 98% percentile ($p_{98}$) and the 99.95% percentile ($p_{99.95}$) of the intensity values. Then the patch is separated into three channels: first, we copy the whole patch into channels 1, 2, and 3; second, the intensity values in channels 1, 2, and 3 are clamped to the ranges $p_2$ to $(p_2+p_{98})/2$, $(p_2+p_{98})/2$ to $p_{98}$, and $p_{98}$ to $p_{99.95}$, respectively; and finally each channel is normalized to the −1 to 1 range. As discussed later, this heuristic improves some of our results.

For each Pre-CT patch, the intensity values are also clamped to the range between the bottom 1% and the top 1% voxel values. Then the patch is normalized to the −1 to 1 range.

Evaluation

The quality of the artifact-corrected images is evaluated quantitatively by comparing the segmentations of scala-tympani (ST), scala-vestibuli (SV), and modiolus (MOD) obtained with PreCTseg applied to the real Pre-CTs with the results obtained when applying PreCTseg cannot be directly applied to Post-CTs due to the strong artifacts produced by the electrodes [12] to the artifact-corrected CTs. The output of PreCTseg are surface meshes of the ST, SV, and MOD that have a pre-defined number of vertices. There are 3344, 3132, and 17947 vertices on the ST, SV, and MOD surfaces, respectively, for a total of 24423 vertices. Point-to-point errors (P2PEs), computed as the Euclidean distance in millimeter, between the corresponding vertices on the meshes generated from the real Pre-CTs and the meshes generated from artifact-corrected images are calculated to quantify the quality of the artifact-corrected images.

To compare the method to the state of the art, we also segment ST, SV, and MOD using a library-based method proposed by Reda et al. [24] in Post-CTs. The output of the library-based method are surface meshes for ST, SV, and MOD that have the same anatomical correspondences as the meshes generated by PreCTseg. The P2PEs between the corresponding vertices on the meshes generated from real Pre-CTs by using PreCTseg and the meshes generated from Post-CTs by using the library-based method are calculated and serve as baseline for comparison.

To evaluate the band-wise intensity normalization approach, we train the cGAN with and without such pre-processing step, and compare the results that are generated with each strategy.

Experiments

In certain embodiments, the PyTorch implementation of the cGAN proposed by Isola et al. [7] is used in our experiments. Since the cGAN is a 2D network, we train our cGAN on the axial view of the CTs. Input images are 2D 3-channel images, each of those is a slice of the 3D 3-channel Post-CT patch. As the current implementation of the cGAN requires the number of input and output channels to be the same, the target images of the cGAN are 2D 3-channel images in which each channel is identical and is the patch's slice in the Pre-CT that matches the patch's slice in the Post-CT used as input. In total 14346 paired Pre-CT and Post-CT 2D slices are used for training. To augment the number of training pairs, each slice is resized to 256×256 pixels and then padded to 286×286 pixels. Sub-images of 256×256 pixels are randomly cropped at the same location in the paired Pre- and Post-CT slices during the training. Horizontal flipping of the training pairs is also applied during the training to further augment the number of training pairs. The default value of λ=100 is used to weigh the L1 distance loss. The cGAN is trained alternatively between one stochastic gradient descent (SGD) step on D, then one step on G, using minibatch size of 1 and the Adam solver [8] with momentum 0.5. The cGAN is trained for 200 epochs in which a fixed learning rate of 0.0002 is applied in the first 100 epochs, and a learning rate that is linearly reduced to zero in the second 100 epochs. The output of D, which is recorded every 100 iterations in each epoch, represents the probability that an image is real rather than fake. D is unable to differentiate between the real and the fake images when the output of D is 0.5 [4]. For each epoch, we calculate the median of the outputs of D and the model that is saved at the epoch in which the median is the closest to 0.5 among the 200 epochs is used as our final cGAN model. At the testing phase, the cGAN processes the testing 3D Post-CTs patches slice by slice, then the artifact-corrected slices are stacked to create 3D patches. These 3D patches are resized to their original sizes and translated back to their original spatial locations in the Post-CTs. Then we use PreCTseg to segment ST, SV, and MOD in these images.

Results

Figure 3A:
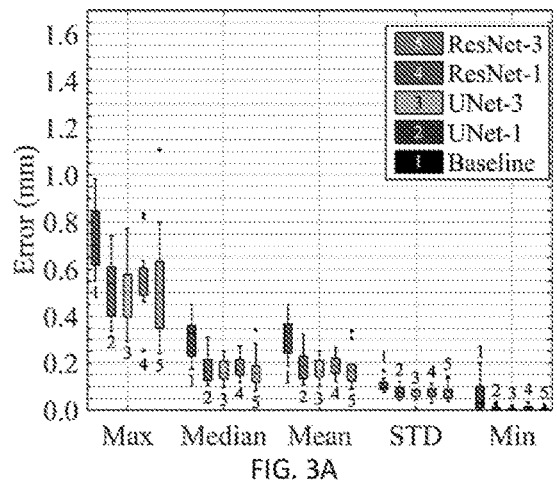
FIGS. 3A-3C show boxplots of P2PEs of the 74 ears (FIG. 3A), the 62 ears scanned by the conventional scanners (FIG. 3B), and the 12 ears scanned by the low-dose scanners (FIG. 3C), respectively, according to embodiments of the invention.

For each testing ear, we calculate the P2PEs of the 24423 vertices, and we calculate the maximum (Max), mean, median, standard deviation (STD), and minimum (Min) of the P2PEs. FIG. 3A shows the boxplots of these statistics for the 74 testing ears, wherein Baseline denotes segmenting the intra-cochlear anatomical structures in Post-CTs using the library-based method, Unet-1 denotes using UNet as the generator of the cGAN but without the band-wise intensity normalization (BWN), Unet-3 denotes using UNet with the BWN, ResNet-1 denotes using ResNet without the BWN, and ResNet-3 denotes using ResNet with the BWN. The means of Max, median, and STD of the P2PEs of the five approaches are shown in Table 1-1.

TABLE 1-1

The means of Max, median, and STD of the P2PEs of the five approaches (mm).

|  | ResNet-3 | ResNet-1 | UNet-3 | UNet-1 | Baseline |
| --- | --- | --- | --- | --- | --- |
| Max | 0.575 | 0.599 | 0.625 | 0.660 | 0.912 |
| Median | 0.191 | 0.211 | 0.214 | 0.225 | 0.409 |
| STD | 0.084 | 0.085 | 0.091 | 0.097 | 0.133 |

Table 1-1 and the plots show that the cGAN-based methods substantially reduce the P2PEs obtained with the baseline approach. The median of the baseline method is 0.366 mm, whereas the median of ResNet-3 is 0.173 mm, which is less than the half of that of the baseline method. We perform paired t-tests on the Max, median, and STD values of the baseline method between cGAN-based methods, the results show that the cGAN-based methods significantly reduce the P2PEs compared to the baseline method for Max, median, and STD (p<0.05). We also perform paired t-tests between the four cGAN-based approaches. ResNet-3 leads to the lowest median error among the four. Pairwise t-tests show that the difference is statistically significant (p<0.05). There is a substantial but not statistically significant difference between the Max and STD of ResNet-3 and of the other three approaches (p>0.05). For ResNet, applying BWN results in statistically significant lower point-to-point median errors (p<0.05). There is a visible but not statistically significant difference between the medians of UNet-3 and UNet-1 (p>0.05). These results show that BWN affects the architectures differently but comparing the boxplots of UNet-3 and UNet-1, and those of ResNet-1 and ResNet-3, it is apparent that the interquartile ranges of the distributions is reduced when applying BWN.

Figure 3B:
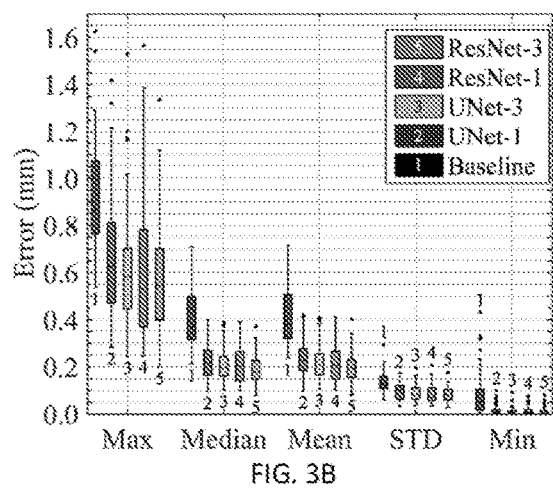
Figure 3C:
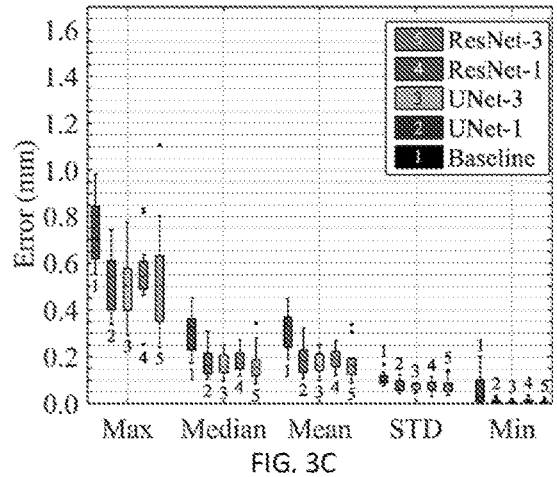

FIG. 3B shows the boxplots of the 62 1CTs, which show the same trend as FIG. 3A. FIG. 3C shows the boxplot of the 12 cCTs, it also shows the same trend except that the interquartile ranges of the distributions are not reduced when applying the BWN. It could be that the BWN approach does not generalize well to all image types but we also note that we only have 8 1CTs in the training set and 12 1CTs in the testing set. It is thus difficult to draw hard conclusions at this point. We are acquiring more data to address this issue.

Figure 4A:
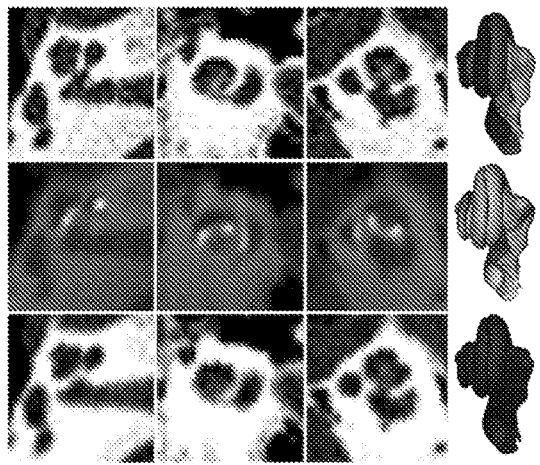
FIGS. 4A-4C shows three example cases in which the invented method (ResNet-3) achieves best (FIG. 4A), average (FIG. 4B), and poor (FIG. 4C) performances, respectively, according to embodiments of the invention. The left, middle, and right column of each case show the axial, coronal, and sagittal views of the 3D patches.
Figure 4B:
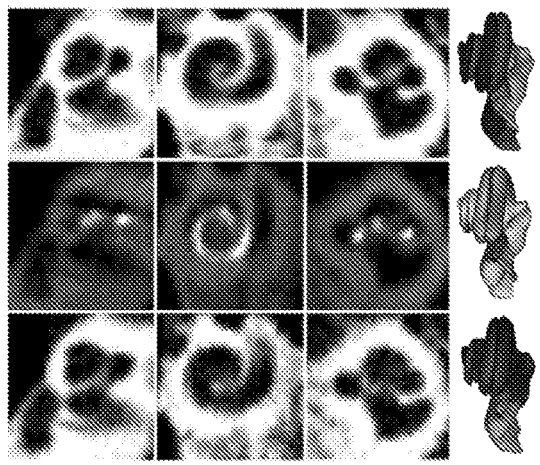
Figure 4C:
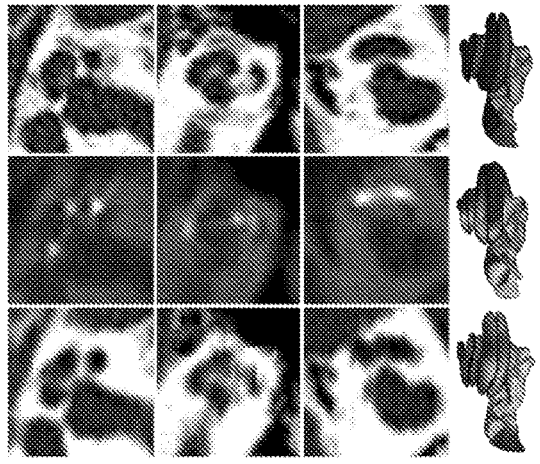

FIGS. 4A-4C shows three example cases in which the invented method (ResNet-3) achieves best (FIG. 4A), average (FIG. 4B), and poor (FIG. 4C) performances, respectively, in the sense of the medians of the P2PEs. For each case, the top row shows three orthogonal views of the Pre-CT and the meshes generated when applying the active shape model-based method [12] to this CT. The ST, SV, and MOD surfaces are shown in red, blue, and green, respectively. The middle row shows the Post-CT and the meshes generated when applying the library-based method to this CT. The bottom row shows the output of cGAN and the meshes generated when applying the active shape model-based method to this image. The meshes in the middle and the bottom rows are color-coded with the P2PE at each vertex on the meshes. These images confirm the results presented in FIGS. 3A-3C. Notably, even in the worst case, segmentation errors are on the order of 0.2 mm for a large portion of the structures. We also note that the output images of cGAN show good slice-to-slice consistency, i.e., there is no "jaggedness", in the coronal and the sagittal views, although the cGAN is a 2D network and it is trained on the axial view only.

The library-based method proposed by Reda et al. [24] has also been applied to these artifact-corrected images. The results are better than with the artifact-affected images but statistically worse than those obtained with PreCTseg on the synthetic images.

Briefly, in the first exemplary example, we disclose, among other things, an approach for localizing the ICA in the Post-CT images, which uses 2D cGANs to synthesize pre-operative images from post-operative images. This permits to use segmentation algorithms designed to operate on Pre-CT images even when these are not available. The method is capable of removing metallic artifacts in CT ear images of CI recipients. The method is tested on a large dataset, and shows significantly reduction of the segmentation error for intra-cochlear structures in post-operative images when compared to the current state-of-the-art approach. The method according to the invention can be potentially used for MAR in CTs at other body sites. It would also be interesting to explore the possibility of applying such idea to correct various types of artifact in other types of medical images.

Example 2

Metal Artifact Reduction for Segmentation of the Intra Cochlear Anatomy in CT Ear Images with 3D cGAN In this second exemplary example, we expand on our method of EXAMPLE 1 by moving from a 2D architecture to a 3D architecture. We perform a large validation and comparative study that shows that the 3D architecture improves significantly the quality of the synthetic images measured by the commonly used mean structural similarity index (MSSIM) [7]. In this example, we increase the size of the testing dataset to 124 ears and explore ways to improve our method further by (1) using a 3D architecture rather than a 2D architecture and (2) modifying the training objective of the 3D-cGANs, which is a sum of an adversarial loss and an L1 reconstruction loss. The quality of the artifact-corrected images is evaluated quantitatively by computing the surface error between the segmentations of the ICA obtained with PreCTseg applied to the real Pre-CT images and to the artifact-corrected CT images. We further validate our method by comparing the ICA obtained with PreCTseg applied to the artifact-corrected CTs and those which are obtained with PostCTseg1 and PostCTseg2 directly applied to the Post-CT images. Finally, as is commonly done to assess the quality of images, we compare the MSSIM between the real images and the synthetic images obtained with the 2D and 3D architectures, which shows that the segmentation results obtained with the 3D architecture are better than those obtained with the 2D architecture although differences have not reached statistical significance.

Training Objectives

Adversarial loss: For the purpose of eliminating the artifacts produced by the CI, we use cGANs that are conditioned on the artifact-affected Post-CT images. G thus produces an artifact-free image $G(x)$ from a Post-CT image x, and $G(x)$ should not be distinguishable from the real artifact-free Pre-CT image y by D, which is trained to do as well as possible to detect G's "fakes". The output of D can be interpreted as the probability of an image to be generated by G rather than a true Pre-CT image. Therefore, the training objective of D is to assign a high value to $G(x)$ and a low value to y. Conversely, the training objective of G is to fool D to assign a low value to $G(x)$ and a high value to y. Thus, the adversarial loss of the cGANs can be expressed as:

$$L_{cGAN}(G, D) = \min_G \max_D \mathbb{E}_{x,y}[\log(D(x, y))] + \mathbb{E}_x[\log(1 - D(x, G(x)))] \quad (2\text{-}1)$$

Reconstruction loss: Previous research suggests that it is beneficial to mix the adversarial loss with a more traditional reconstruction loss, such as the L1 distance between $G(x)$ and y [7], which is defined as:

$$L_{L_1}(G) = \mathbb{E}_{x,y}[\|y - G(x)\|_1] \quad (2\text{-}2)$$

For the ultimate purpose that is to localize the ICA in the Post-CT images, we are more concerned about the quality of the image content in the small region that encompasses the cochlea than in the other regions in an artifact-corrected CT, therefore we assign a higher weight to the voxels inside this region when calculating the L1 loss. To do so, we first create a bounding box that encloses the cochlea. With the number of voxels inside the bounding box equal to $N_{in}$ and the number of voxels outside of the bounding box equal to $N_{out}$, we assign weights to the voxels inside and outside of the bounding box that are equal to $(N_{in}+N_{out})/N_{in}$ and 1, respectively. The weighted L1 (WL1) loss can then be expressed as shown in Equation (2-3):

$$L_{WL_1}(G) = \mathbb{E}_{x,y}[\|W \circ (y - G(x))\|_1] \quad (2\text{-}3)$$

wherein W is the weighting matrix and $\circ$ is the element-wise multiplication operation.

Total loss: The total loss can be expressed as a combination of the adversarial loss and the reconstruction loss:

$$L = \arg\min_G \max_D L_{cGAN}(G, D) + \alpha L_{WL_1}(G) \quad (2\text{-}4)$$

wherein $\alpha$ is the weight of the WL1 term.

Architecture of the 3D-cgans

Figure 5:
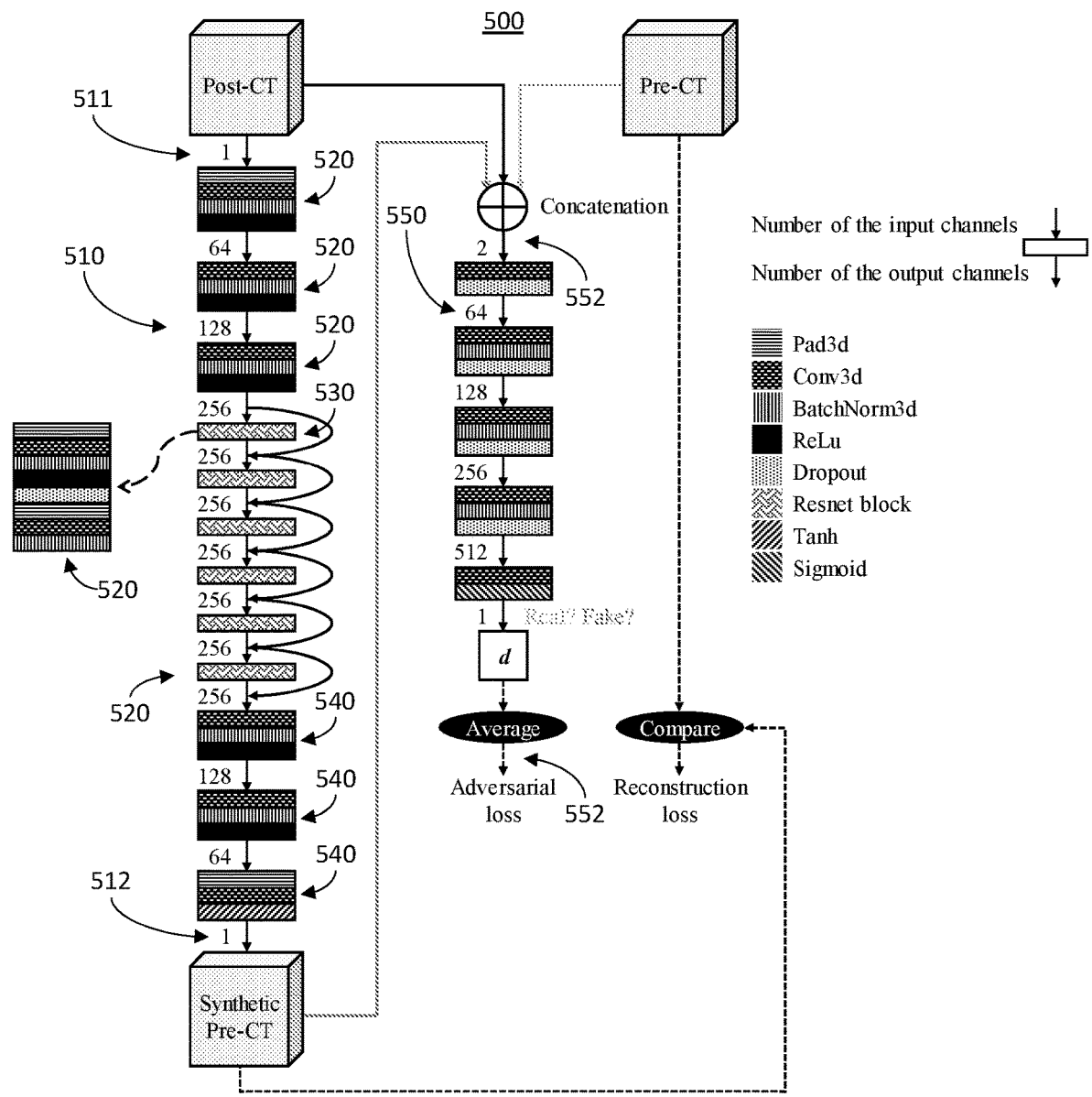
FIG. 5 shows schematically the architecture of the 3D-cGANs, according to embodiments of the invention.

FIG. 5 shows the architecture 500 of the 3D-cGANs according to one embodiment of the invention. The generator 510 is a 3D network which includes 3 convolutional blocks 520 followed by 6 ResNet blocks 530 [5], and another 3 convolutional blocks 540 (FIG. 5, the sub-network on the left). As is done in Isola et al. [7], dropout is applied to introduce randomness into the training of the generator 510. The input 511 of the generator 510 is a 1-channel 3D Post-CT image, and the output 512 is a 1-channel 3D synthetic Pre-CT image. The discriminator 550 is a fully convolutional network (FIG. 5, the sub-network on the right) that maps the input 551, which is the concatenation of a Post-CT image and the corresponding Pre-CT image (or a Post-CT image and the synthetic Pre-CT image), to a 3D array d, where each $d_{i,j,k}$ captures whether the (i,j,k)-th 3D patch of the input is real or fake. The ultimate output 552 of the discriminator 550 is a scalar obtained by averaging d.

Dataset

In this exemplary study, the dataset includes Post-CT and Pre-CT image volume pairs of 252 ears. It should be noted that Pre-CT and Post-CT image volume pairs of other numbers of ears (or other regions of a living subject) can also be utilized to practice the invention. All these CT volumes have been acquired with the CIs recipients in roughly the same position. 24 Post-CT images and all of the 252 Pre-CT images were acquired with several conventional scanners referred to as cCT scanners (GE BrightSpeed, LightSpeed Ultra; Siemens Sensation 16; and Philips Mx8000 IDT, iCT 128, and Brilliance 64). The other 228 Post-CT images were acquired with a low-dose flat-panel volumetric CT scanner referred to as 1CT scanner (Xoran Technologies xCAT® ENT). The typical voxel size is and $0.25 \times 0.25 \times 0.3$ mm$^3$ for the cCT images, and $0.4 \times 0.4 \times 0.4$ mm$^3$ for the 1CT images. The 252 ears are randomly partitioned into a set of 90 ears for training, 25 ears for validation, and 137 ears for testing. After random assignment, there are 13 bilateral cases for which one ear has been assigned to the training (or validation) set and the other ear has been assigned to the testing set, the 13 ears of such cases are removed from the testing set so that no image from the same patient are used for both training and testing. Details about the image set are listed in Table 2-1.

TABLE 2-1

The number of ears and the type of CT scanner used to acquire the images in the training, validation, and testing sets. "lCT-cCT" denotes that the ear has been scanned by the lCT scanner postoperatively and a cCT scanner preoperatively, and "cCT-cCT" denotes that the ear has been scanned by a cCT scanner postoperatively and preoperatively.

| Usage | Total number of the ears | Number of Post- and Pre-CT pairs | |
|---|---|---|---|
| | | lCT-cCT | cCT-cCT |
| Training | 90 | 82 | 8 |
| Validation | 25 | 21 | 4 |
| Testing | 124 | 88 IB ears | 78 | 10 |
| | | 36 IU ears | 34 | 2 |

The Pre-CT images are registered to the Post-CT images using intensity-based affine registration techniques [9, 18]. The registrations have been visually inspected and confirmed to be accurate. We apply image augmentation to the training set by rotating each image by 20 small random angles in the range of −10 and 10 degrees about the x-, y-, and z-axis, such that 60 additional training images are created from each original image. This results in a training set that is expanded to 5490 volumes.

Figures 6A, 6B:
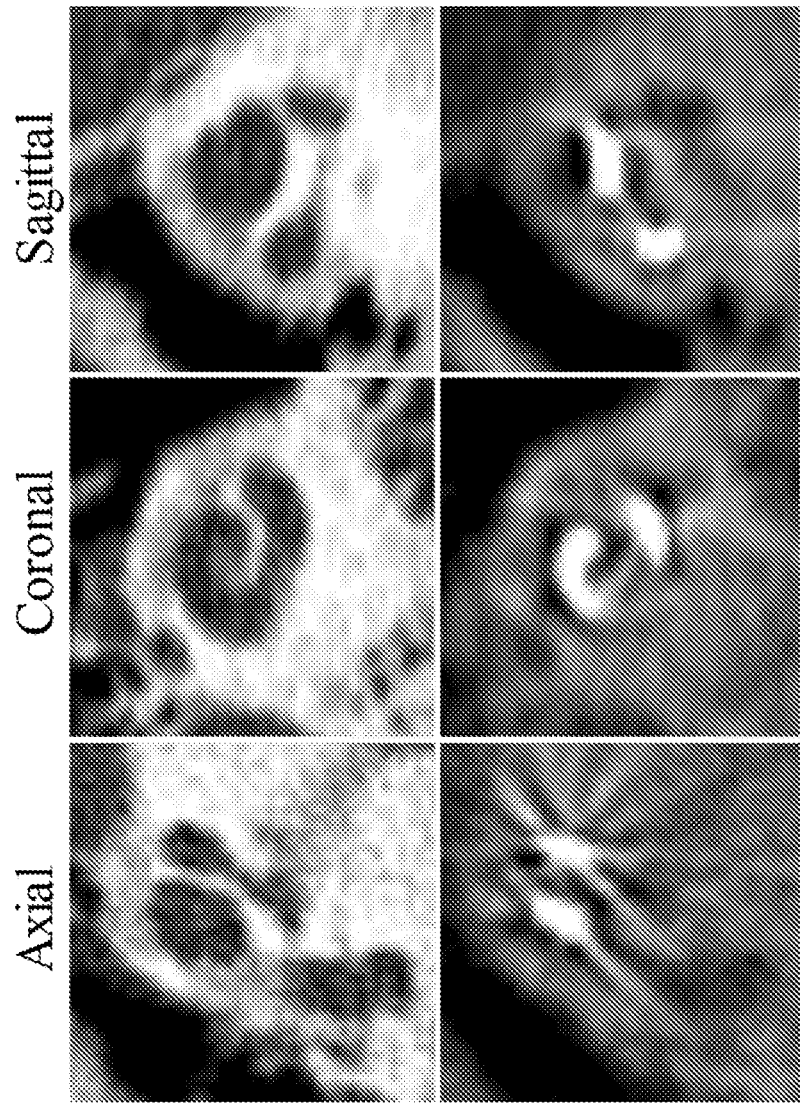
FIGS. 6A-6B shows three orthogonal views of the Pre-CT (FIG. 6A) and the Post-CT (FIG. 6B) of an example ear.

Because in the dataset the typical voxel size of the Post-CT images is 0.4×0.4×0.4 mm$^3$, we first resample the CTs to 0.4×0.4×0.4 mm$^3$, so that all of the images have the same resolution. 3D patch pairs that contain the cochlea are cropped from the Pre-CT and Post-CT images, i.e., paired patches contain the same cochlea; one patch with and the other without the implant (FIGS. 6A-6B). The size of the patches is 38.4×38.4×38.4 mm$^3$ (96×96×96 voxels). Each patch is clamped to the range 0.1-th to 99.9-th percentiles of its intensity values. Then the patches are rescaled to the −1 to 1 range.

Optimization and Inference

In certain embodiments, the PyTorch implementation of the 3D-cGANs is adapted from the 2D implementation provided by Zhu et al. [23]. $\alpha$ introduced in Eq. (2-4) is set to its default value 100. In practice, the cochlea is at the center of each 3D patch and we simply use the central 56×56×56 voxels of the 3D patch as the bounding box for calculating the weights. The 3D-cGANs are trained alternatively between one stochastic gradient descent step on the discriminator, then one step on the generator, using a mini-batch size of 1 and the Adam solver [8] with momentum 0.5. The 3D-cGANs are trained for 200 epochs in which a fixed learning rate of 0.0002 is applied in the first 100 epochs and a learning rate that is linearly reduced to zero in the second 100 epochs. At the inference phase, given an unseen Post-CT patch, the generator produces an artifact-corrected image.

The MSSIM inside the 56×56×56 bounding box of the true Pre-CT images and the artifact-corrected CTs generated by the cGANs has been used to select the number of training epochs. To do so we run inference on the validation set every 5 epochs, the MSSIM is calculated for each of the ears, and the epoch where it achieves the highest median MSSIM is selected as the optimal epoch.

Evaluation

The present method is compared to the baseline methods, PostCTseg1 and PostCTseg2, as well as to the 2D-cGANs-based method disclosed in EXAMPLE 1. We upsample the voxel size of the CTs to 0.1×0.1×0.1 mm$^3$ to train and test the 2D-cGANs. This was done to improve slice-to-slice consistency. Due to memory limitations, this is not possible for the 3D-cGANs that are trained with volumes.

To evaluate the quality of the synthetic images independently from the segmentation results we compare the MSSIM between the original pre-CT images and the images produced with the 2D and 3D architectures. We also compare the performance of the 3D-cGANs trained using the weighted L1 loss and those which are trained using the original L1 loss.

Point-to-Point Errors (P2PEs)

The effect of artifact reduction on segmentation accuracy is evaluated quantitatively by comparing the segmentation of the structures of interest (the ST, SV, and MOD) obtained with PreCTseg applied to the real Pre-CT images with the results obtained when applying PreCTseg to the artifact-corrected CT images. Because PreCTseg is based on an active shape model approach, the outputs of PreCTseg are surface meshes of the ST, SV, and MOD that have a pre-defined number of vertices, and each vertex corresponds to an anatomical location on the surface of the structures. There are 3344, 3132, and 17947 vertices on the ST, SV, and MOD surfaces, respectively, for a total of 24423 vertices. Point-to-point errors (P2PEs), computed as the Euclidean distance in millimeter, between the corresponding vertices on the meshes generated from the real Pre-CT images and the meshes generated from artifact-corrected images are calculated to quantify the quality of the artifact-corrected images.

To compare the P2PEs of the 3D-cGANs-based method to results obtained with the baseline methods, we segment the ST, SV, and MOD with PostCTseg1 and PostCTseg2 in the Post-CT images of the IU ears and the IB ears, respectively. The output of PostCTseg1 and PostCTseg2 are surface meshes for the ST, SV, and MOD that have the same anatomical correspondences as the meshes generated by PreCTseg. The P2PEs between the corresponding vertices on the meshes generated with PreCTseg in the real Pre-CT images and the meshes generated with PostCTseg1 and PostCTseg2 in the Post-CT images serve as baselines for comparison.

To compare the 3D-cGANs-based method to our previous 2D-cGANs-based method, the P2PEs between the corresponding vertices on the meshes generated from the real Pre-CT images with PreCTseg and the meshes generated from artifact-corrected images generated by the 2D-cGANs with PreCTseg are also calculated.

Mean Structural Similarity (MSSIM)

To compare the quality of the artifact-corrected images produced by the 2D-cGANs in EXAMPLE 1 and those which are generated by the 3D-cGANs, we compare the MSSIM inside the 56×56×56 bounding box of the true Pre-CT images and the artifact-corrected CTs generated by the 2D-cGANs and the 3D-cGANs. The MSSIM between the true Pre-CT images and the Post-CT images serves as the baseline for comparison. The MSSIM between the artifact-corrected CT image G(x) and the true Pre-CT image y can be expressed as:

$$MSSIM(G(x), y) = \frac{1}{M} \sum_{j=1}^{M} SSIM(g_j, y_j) \qquad (2\text{-}5)$$

wherein SSIM($g_j$, $y_j$) is the local structural similarity (SSIM) between $g_j$ and $y_j$, which are the image contents at the j-th local window of G(x) and y, and M is the number of local windows in the image. The local SSIM can be expressed as:

$$SSIM(g_j, y_j) = \frac{(2\mu_{g_j}\mu_{y_j} + C_1)(2\sigma_{g_j y_j} + C_2)}{(\mu_{g_j}^2 + \mu_{y_j}^2 + C_1)(\sigma_{g_j}^2 + \sigma_{y_j}^2 + C_2)} \quad (2\text{-}6)$$

wherein $\mu_{g_j}$, $\mu_{y_j}$, $\sigma_{g_j}$, $\sigma_{y_j}$, are the local means, standard deviations, and cross-covariance of $g_j$ and $y_j$; $C_1$ and $C_2$ are constants to avoid instability when $\mu_{g_j}^2 + \mu_{y_j}^2$ or $\sigma_{g_j}^2 + \sigma_{y_j}^2$ are close to zero [17].

Results

Figures 7A, 7B, 7C:
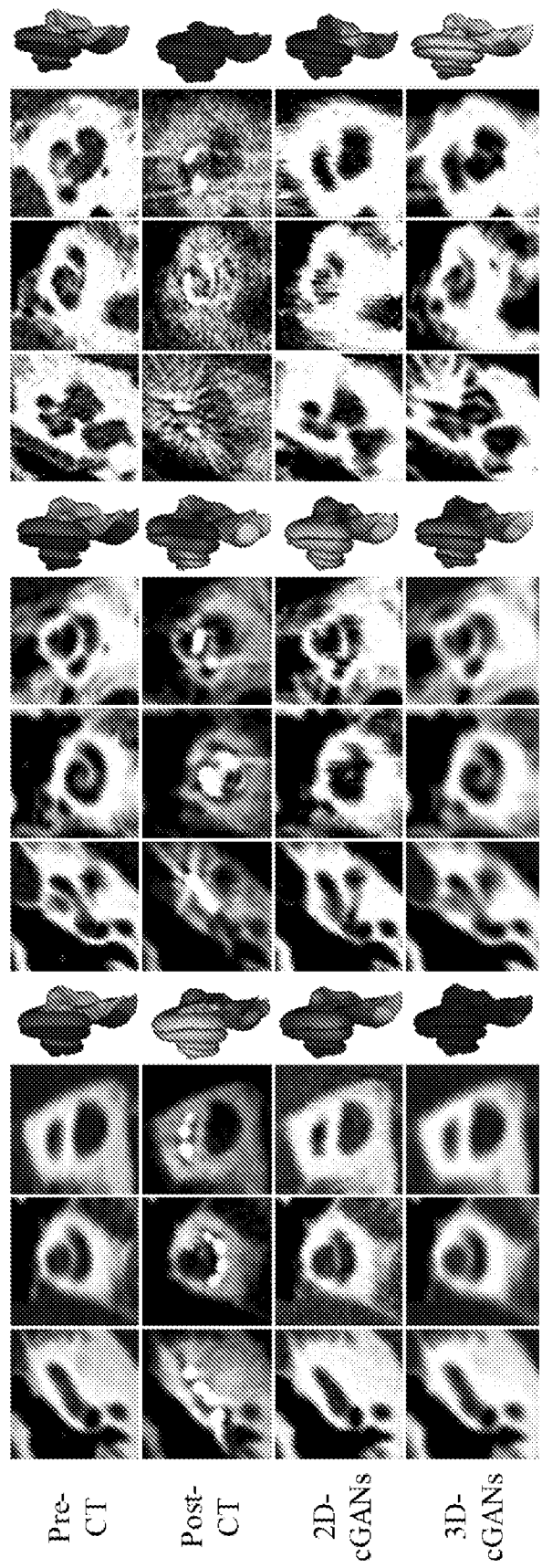
FIGS. 7A-7C shows three example cases in which the invented method leads to good (FIG. 7A), average (FIG. 7B), and poor (FIG. 7C) results, respectively, according to embodiments of the invention.

FIGS. 7A-7C show 3 example cases in which our proposed method leads to (FIG. 7A) good, (FIG. 7B) average, and (FIG. 7C) poor results. For each case, the first row shows three orthogonal views of the Pre-CT image and the meshes generated when applying PreCTseg to this CT. The ST, SV, and MOD surfaces are shown in red, blue, and green, respectively. The second row shows the Post-CT image and the meshes generated when applying PostCTseg2 (or PostCTseg1) to this CT volume. The third and the last rows show the outputs of the 2D-cGANs and the 3D-cGANs and the meshes generated when applying PreCTseg to these images. The meshes from the second to the last rows are color-coded with the P2PE at each vertex on the meshes. Notably, even in the worst case, segmentation errors of the 3D-cGANs are lower than those of the baseline and of the 2D-cGANs. Note also the severity of the artifact in this case and the failure of the segmentation method designed to operate on the post-CT images. The values of the MSSIM and the type of Post-CT and Pre-CT pairs for these examples are listed in Table 2-2. In all cases the MSSIM between the original images and the synthetic images produced by the 3D networks is higher than between the original images and the synthetic images produced by the 2D networks. This is consistent with the visual appearance of the synthetic images as can be appreciated by comparing rows 3 and 4 of FIGS. 7A-7C.

TABLE 2-2

The values of the MSSIM between the true Pre-CT images and the artifact-corrected CT images generated by the 2D-and the 3D-cGANs. "lCT-cCT" denotes that the ear has been scanned by the lCT scanner postoperatively and a cCT scanner preoperatively.

| Image name | Baseline | 2D-cGANs | 3D-cGANs | Type of the Post-CT and Pre-CT pairs |
|---|---|---|---|---|
| FIG. 7A | 0.771 | 0.891 | 0.971 | lCT-cCT |
| FIG. 7A | 0.499 | 0.780 | 0.931 | lCT-cCT |
| FIG. 7A | 0.348 | 0.473 | 0.552 | lCT-cCT |

Point-to-Point Errors (P2PEs)

For each testing ear, we calculate the P2PEs of the 24423 vertices, and we calculate the maximum (Max), mean (Mean), median (Median), standard deviation (STD), and minimum (Min) of the P2PEs.

Figure 8B:
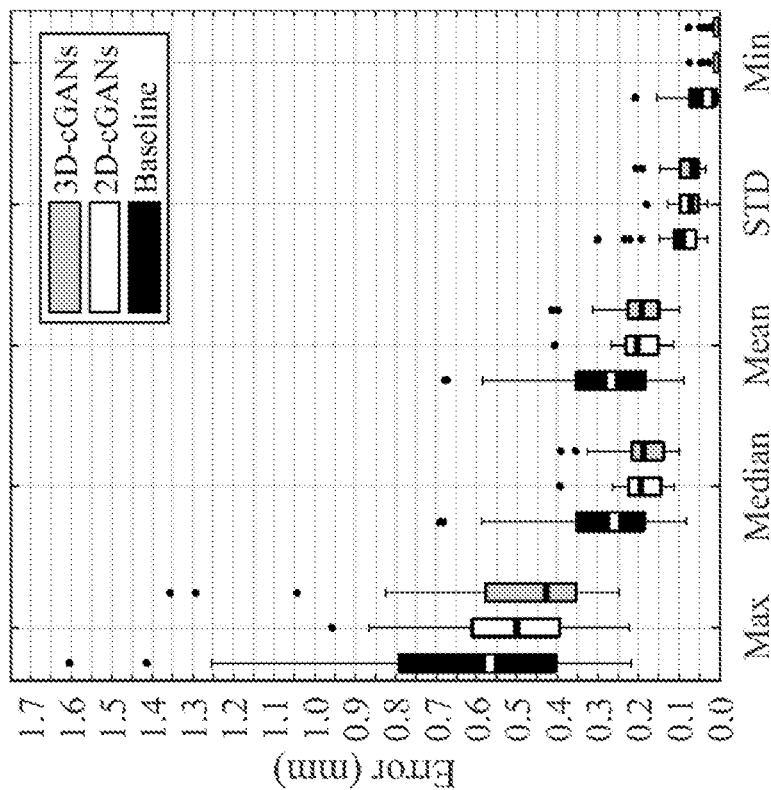
FIG. 8A-8F show boxplots of P2PEs for (FIG. 8A) the 88 IB ears, (FIG. 8B) the 36 IU ears, (FIG. 8C) the 78 IB ears scanned by the 1CT scanner postoperatively and the cCT scanners preoperatively, (FIG. 8D) the 34 IU ears scanned by the 1CT scanner postoperatively and the cCT scanners preoperatively, (FIG. 8E) the 10 IB ears scanned by the cCT scanners postoperatively and preoperatively, and (FIG. 8F) the 2 IU ears scanned by the cCT scanners postoperatively and preoperatively, respectively, according to embodiments of the invention.
Figure 8A:
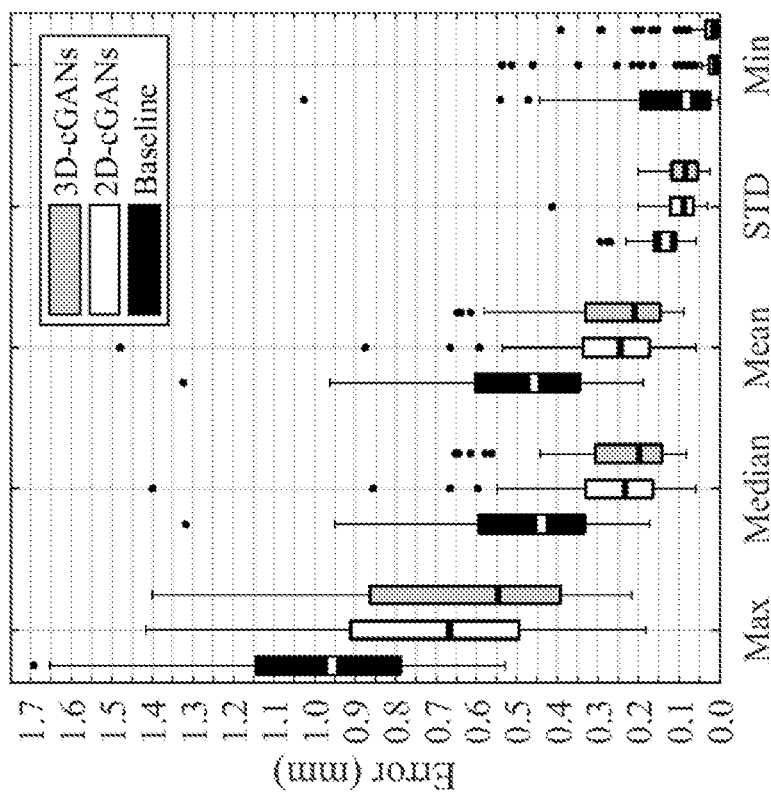

FIGS. 8A-8B show the boxplots of these statistics for the 88 IB ears and the 36 IU ears. PostCTseg2 and PostCTseg1 serve as the baseline method for the bilateral and unilateral cases, respectively. FIG. 8A shows that both the 2D-cGANs and the 3D-cGANs-based methods substantially reduce the P2PEs obtained with PostCTseg2 in the Post-CT images. The median of the baseline method is 0.439 mm, the medians of the 2D-cGANs and the 3D-cGANs-based approach are 0.233 mm and 0.198 mm, which are about half of the baseline method. We perform a Wilcoxon signed-rank test [10] between the Max, Median, Mean, STD, and Min values obtained with the baseline method and the cGANs-based methods, and the resulting p-values are corrected using Holm-Bonferroni method [6]. The results show that the cGAN-based methods significantly reduce the P2PEs compared to the baseline method ($p<0.05$) (Table 2-3. 88 IB ears, row 1 and 2). We also perform a Wilcoxon signed-rank test between the 2D-cGANs and the 3D-cGANs-based approaches that shows that despite being visible the difference between the results of the 2D-cGANs and the 3D-cGANs are not statistically significant ($p>0.05$) (Table 2-3. 88 IB ears, row 3). FIG. 8B shows that both the 2D-cGANs and the 3D-cGANs-based methods reduce the P2PEs obtained with PostCTseg1 in the Post-CT images. The median of the baseline method is 0.260 mm, whereas the medians of the 2D-cGANs and the 3D-cGANs are 0.194 mm and 0.188 mm, respectively. A Wilcoxon signed-rank test shows that the cGANs-based methods significantly reduce the P2PEs compared to the baseline method for Median and Mean ($p<0.05$) (Table 2-3. 36 IU ears, row 1 and 2). There is a visible but not statistically significant difference between the Max of the cGANs-based method and the baseline ($p>0.05$) (Table 2-3. 36 IU ears, row 1 and 2). There is a visible but not statistically significant difference between the results of the 2D-cGANs and the 3D-cGANs ($p>0.05$) (Table 2-3. 36 IU ears, row 3).

Figures 8C, 8D:
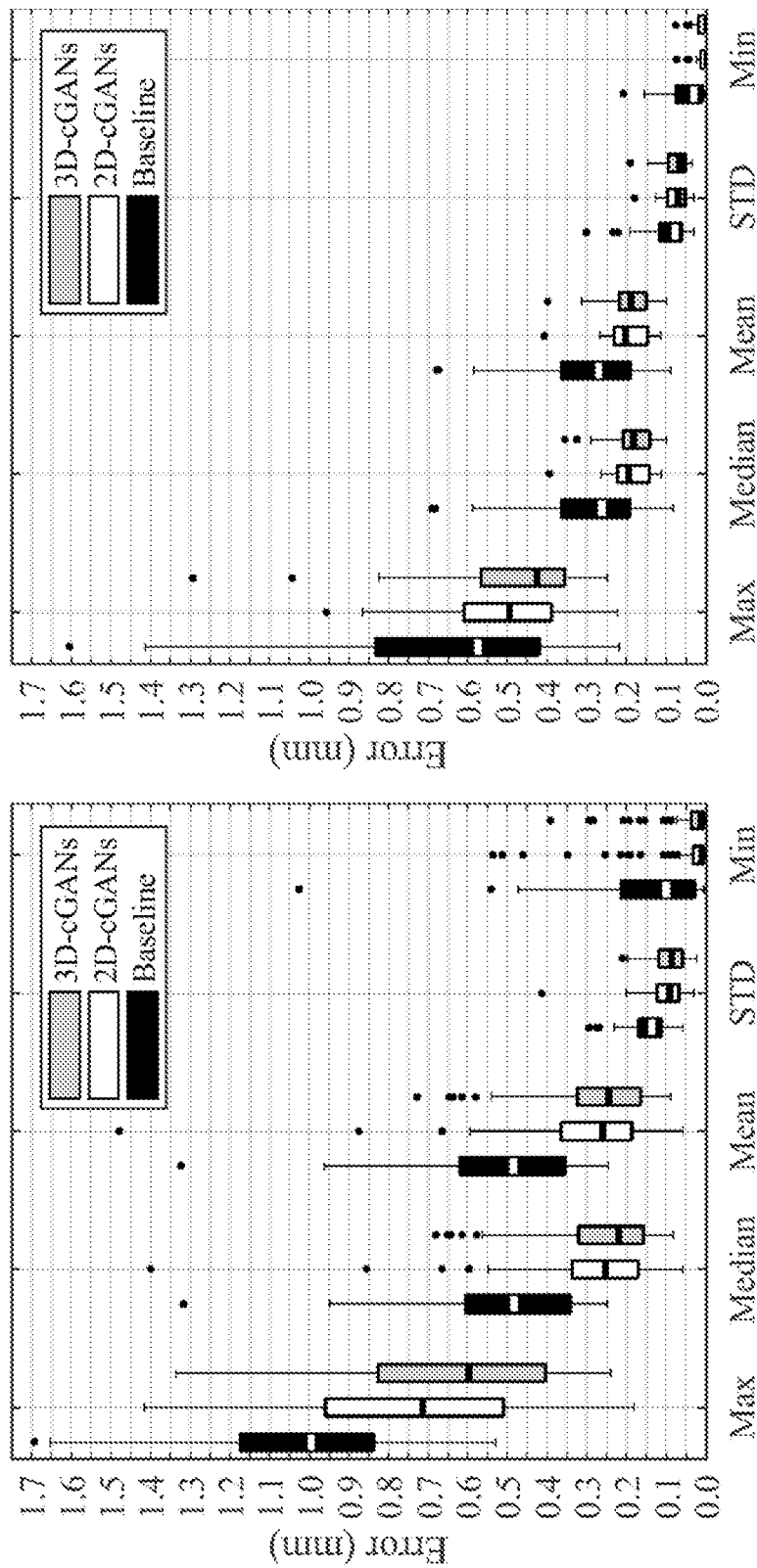

FIGS. 8C-8D show the boxplots of the statistics of the 78 IB ears and the 34 IU ears that have been scanned with the lCT scanner postoperatively and the cCT scanners preoperatively. Table 2-4 shows the results of the Wilcoxon signed-rank tests. These show the same trend as FIGS. 8A-8B and Table 2-3.

Figure 8F:
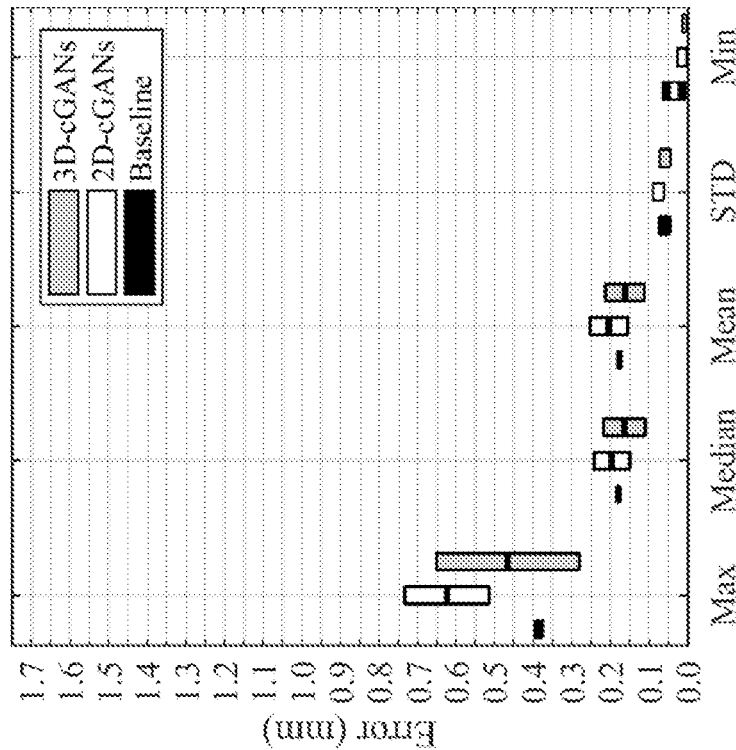
Figure 8E:
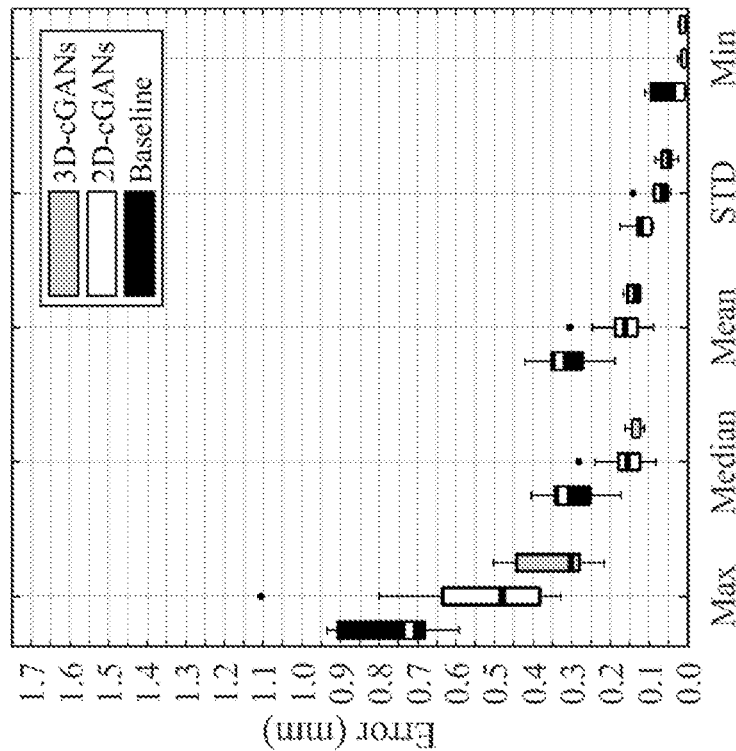

FIGS. 8E-8F show the boxplots of the statistics of the 10 IB ears and the 2 IU ears that have been scanned with the cCT scanners postoperatively and preoperatively. At the time of writing, we are not able to draw strong conclusions form these two plots because we only have a very limited number of such images but the trends are similar to those obtained with the other datasets.

TABLE 2-3

P-values of the two-sided and one-sided Wilcoxon signed-rank tests of the five statistics for the P2PEs of the 88 IB ears and the 36 IU ears.

| Testing ears | Approaches to compare | Max Two-sided | Max One-sided | Median Two-sided | Median One-sided | Mean Two-sided | Mean One-sided | STD Two-sided | STD One-sided | Min Two-sided | Min One-sided |
|---|---|---|---|---|---|---|---|---|---|---|---|
| 88 IB ears | Post-CT + PostCTseg2 2D-cGANs + PreCTseg | <0.001 | <0.001 | <0.001 | <0.001 | <0.001 | <0.001 | <0.001 | <0.001 | <0.001 | <0.001 |

TABLE 2-3-continued

P-values of the two-sided and one-sided Wilcoxon signed-rank tests of the five statistics for the P2PEs of the 88 IB ears and the 36 IU ears.

| Testing ears | Approaches to compare | Max Two-sided | Max One-sided | Median Two-sided | Median One-sided | Mean Two-sided | Mean One-sided | STD Two-sided | STD One-sided | Min Two-sided | Min One-sided |
|---|---|---|---|---|---|---|---|---|---|---|---|
| | Post-CT + PostCTseg2 3D-cGANs + PreCTseg | <0.001 | <0.001 | <0.001 | <0.001 | <0.001 | <0.001 | <0.001 | <0.001 | <0.001 | <0.001 |
| | 2D-cGANs + PreCTseg 3D-cGANs + PreCTseg | 0.117 | — | 0.174 | — | 0.179 | — | 0.628 | — | 1.483 | — |
| 36 IU ears | Post-CT + PostCTseg1 2D-cGANs + PreCTseg | 0.136 | — | <0.001 | <0.001 | <0.001 | <0.001 | 0.371 | — | 0.002 | <0.001 |
| | Post-CT + PostCTseg1 3D-cGANs + PreCTseg | 0.115 | — | 0.002 | 0.001 | 0.002 | 0.001 | 0.221 | — | 0.005 | — |
| | 2D-cGANs + PreCTseg 3D-cGANs + PreCTseg | 0.729 | — | 0.825 | — | 0.949 | — | 0.937 | — | 1.482 | — |

Note:
Bold indicates cases that are significantly different (p-value less than 0.05). The p-values have been corrected using Holm-Bonferroni method.

TABLE 2-4

P-values of the two-sided and one-sided Wilcoxon signed-rank tests of the five statistics of the P2PEs for the 78 IB ears and the 34 IU ears that have been scanned with the lCT scanner postoperatively and the cCT scanners preoperatively

| Testing ears | Approaches to compare | Max Two-sided | Max One-sided | Median Two-sided | Median One-sided | Mean Two-sided | Mean One-sided | STD Two-sided | STD One-sided | Min Two-sided | Min One-sided |
|---|---|---|---|---|---|---|---|---|---|---|---|
| 78 IB ears | Post-CT + PostCTseg2 2D-cGANs + PreCTseg | <0.001 | <0.001 | <0.001 | <0.001 | <0.001 | <0.001 | <0.001 | <0.001 | <0.001 | <0.001 |
| | Post-CT + PostCTseg2 3D-cGANs + PreCTseg | <0.001 | <0.001 | <0.001 | <0.001 | <0.001 | <0.001 | <0.001 | <0.001 | <0.001 | <0.001 |
| | 2D-cGANs + PreCTseg 3D-cGANs + PreCTseg | 0.136 | — | 0.163 | — | 0.172 | — | 0.770 | — | 1.110 | — |
| 34 IU ears | Post-CT + PostCTseg1 2D-cGANs + PreCTseg | 0.080 | — | 0.001 | <0.001 | <0.001 | <0.001 | 0.285 | — | 0.002 | <0.001 |
| | Post-CT + PostCTseg1 3D-cGANs + PreCTseg | 0.075 | — | 0.002 | 0.001 | 0.002 | <0.001 | 0.285 | — | 0.006 | — |
| | 2D-cGANs + PreCTseg 3D-cGANs + PreCTseg | 0.993 | — | 0.590 | — | 0.675 | — | 0.857 | — | 1.110 | — |

Note:
Bold indicates cases that are significantly different (p-value less than 0.05). The p-values have been corrected using the Holm-Bonferroni method.

TABLE 2-5

P-values of the two-sided and one-sided Wilcoxon signed-rank tests of the five statistics for the P2PEs of the 124 testing ears.

| Reconstruction loss to compare | Max | | Median | | Mean | | STD | | Min | |
|---|---|---|---|---|---|---|---|---|---|---|
| | Two-sided | One-sided | Two-sided | One-sided | Two-sided | One-sided | Two-sided | One-sided | Two-sided | One-sided |
| WL1 L1 | 0.004 | 0.002 | <0.001 | <0.001 | 0.001 | <0.001 | <0.001 | <0.001 | 0.945 | — |

Note:
Bold indicates cases that are significantly different (p-value less than 0.05). The p-values have been corrected using Holm-Bonferroni method.

Figure 9:
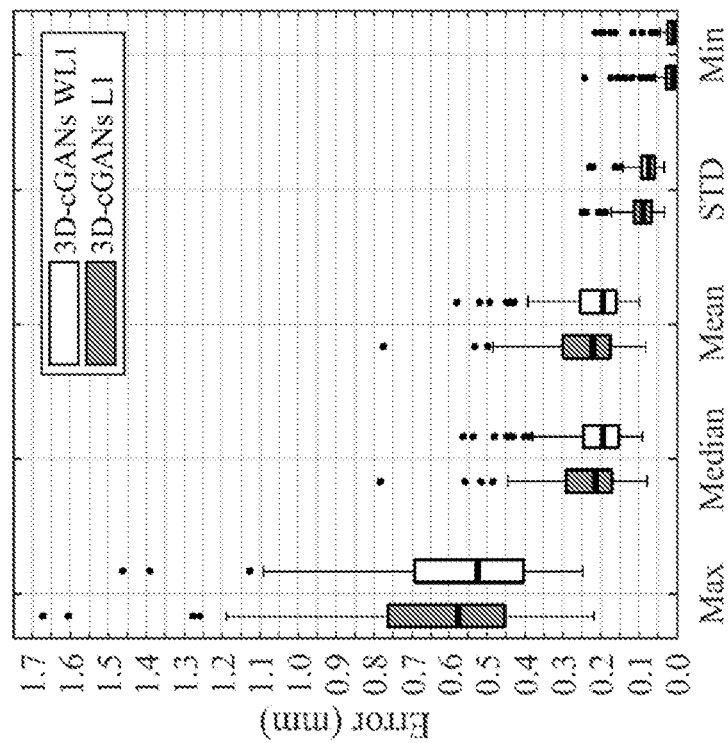
FIG. 9 shows a poxplot of P2PEs for the 124 testing ears. "3D-cGANs WL1" and "3D-cGANs L1" denote the results obtained with the 3D-cGANs which are trained using the weighted L1 loss and original L1 loss, respectively, according to embodiments of the invention.

FIG. 9 shows the boxplots of the statistics for P2PEs of the 124 testing ears processed by the 3D-cGANs that are trained using L1 and WL1. Visually, the medians of the Max, Median, and Mean error values obtained with WL1 (yellow bars) are lower than those obtained with L1 (black bars). Wilcoxon signed-rank tests reported in Table 5 show that these differences are significant for the Max, Median, Mean, and STD ($p<0.05$).

Mean Structural Similarity (MSSIM)

Figure 10:
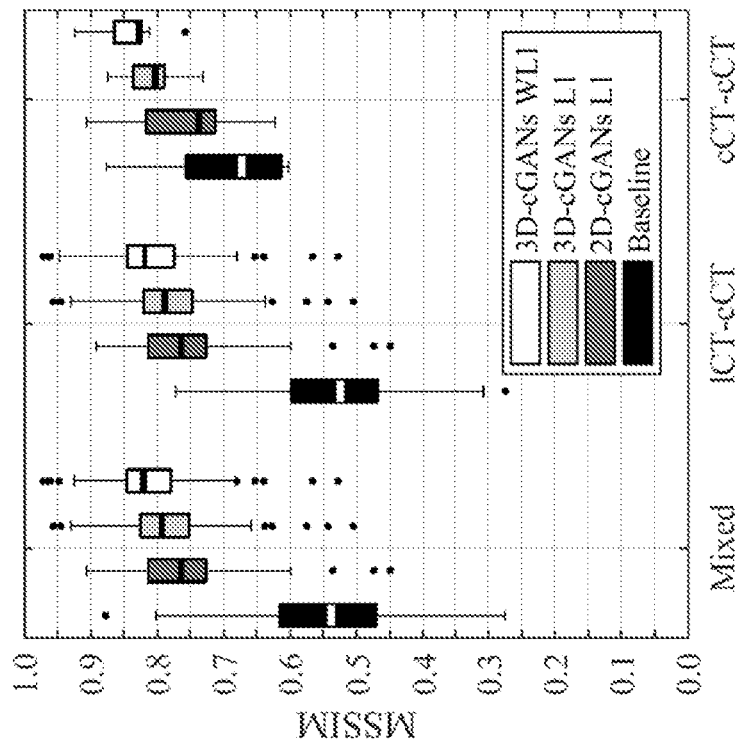
FIG. 10 shows boxplots of the MSSIM for the 124 testing ears (Mixed) (left), the 112 ears scanned by the 1CT scanner postoperatively and the cCT scanners preoperatively (1CT-cCT) (middle), and the 12 ears scanned by the cCT scanners postoperatively and preoperatively (cCT-cCT) (right), respectively, according to embodiments of the invention. "Baseline" denotes the MSSIM between the Post-CT images and the true Pre-CT images; "2D-cGANs L1" denotes the results produced by our previous 2D-cGANs trained with the pure L1 loss; "3D-cGANs L1" and "3D-cGANs WL1" denote the results produced by the 3D-cGANs which are trained using the pure L1 loss and the weighted L1 loss, respectively.

FIG. 10 shows boxplots of the MSSIM for the 124 testing ears. Wilcoxon signed-rank tests show that all of the cGANs-based methods achieve statistically significant higher MSSIM compared to the baseline ($p<0.05$). Table 2-6 shows the p-values of the Wilcoxon signed-rank tests between the results of the 2D-cGANs and the 3D-cGANs that are trained using a different reconstruction loss. The 3D strategies achieve statistically significant higher MSSIM compared to the 2D approach ($p<0.05$). The 3D-cGANs trained with the weighted L1 loss produce a significantly higher MSSIM than those trained with the non-weighted L1 loss ($p<0.05$). We also observe that the 3D-cGANs reach the optimal epoch at the 15-th training epoch when the weighted L1 loss is applied. However, they need 70 training epochs to reach the optimal epoch when the non-weighted L1 loss is applied. This suggests that using weights can accelerate the optimization of the networks.

TABLE 2-6

The p-values of the two-sided and one-sided Wilcoxon signed-rank tests between the MSSIM of the true Pre-CT images and the synthetic images produced by the 2D-cGANs and the 3D-cGANs trained using different reconstruction losses. "1CT-cCT" denotes that the ear has been scanned by the 1CT scanner postoperatively and a cCT scanner preoperatively, and "cCT-cCT" denotes that the ear has been scanned by a cCT scanner postoperatively and preoperatively.

| Approaches to compare | Mixed (124 ears) | | 1CT-cCT (112 ears) | | cCT-cCT (12 ears) | |
|---|---|---|---|---|---|---|
| | Two-sided | One-sided | Two-sided | One-sided | Two-sided | One-sided |
| 2D-cGANs L1 3D-cGANs L1 | <0.001 | <0.001 | <0.001 | <0.001 | <0.001 | <0.001 |
| 2D-cGANs L1 3D-cGANs WL1 | <0.001 | <0.001 | <0.001 | <0.001 | <0.001 | <0.001 |
| 3D-cGANs L1 3D-cGANs WL1 | <0.001 | <0.001 | <0.001 | <0.001 | <0.001 | <0.001 |

Note:
Bold indicates cases that are significantly different (p-value less than 0.05). The p-values have been corrected using Holm-Bonferroni method.

Discussion and Conclusion

As discussed in the recent review article by Yi et al. [19], GANs have been extensively used to solve medical imaging related problems such as classification, detection, image synthesis, low dose CT denoising, reconstruction, registration, and segmentation. However, to the best of our knowledge, GANs have not been proposed to eliminate or reduce metallic artifacts in CT images. There is also a large body of work aiming at reducing artifacts in CT images [2]. But, compared to the existing methods, which generally necessitate the raw data from CT scanners, the approach according to the invention is a post-reconstruction processing method for which the raw data is not required. Compared to other machine-learning-based methods proposed for the removal of metallic artifacts that either depend on existing traditional methods or require post-processing of the outputs produced by machine learning models [3, 14, 21], the method according to the invention is unique in being able to synthesize directly an artifact-free image from an image in which artifacts are present. In addition, our method could also be applied to other types of images affected by the same type of artifacts if sufficient training images including pairs of images with and without artifacts were available. We also hypothesize that if the problems are similar enough transfer learning could be used to reduce the size of the dataset needed for training.

The results we have generated show that the quality of the images produced by the 3D networks is better than that of the images produced by the 2D networks when the MSSIM is used to compare them. This is confirmed by the visual appearance of the synthetic images produces by these two architectures as shown in FIGS. 7A-7C. There is also a small but not statistically significant difference in the segmentation results produced with the images generated with the 3D and the 2D networks; this difference is especially noticeable for the maximum error. The fact that the segmentation results improve only modestly when the quality of the images improves more substantially suggests that the constraints imposed by the active shape model are able to compensate for imperfections in the synthetic images. It is likely that segmentations methods that do not impose strong constraints on the shape for the ICA structures would be more sensitive to those errors. As discussed earlier, we also note that the technique we have developed to assist audiologists in programing the implant depends on the position of the contacts with respect to the anatomy [13]. Any improvement in segmentation accuracy, even small, may have a positive impact on programming recommendations we provide to the audiologists. Assessing the effect of the method we use to eliminate the artifact on these recommendations, i.e., assessing whether or not recommendations would be different if the 2D or 3D version is used, is part of our plans. Finally, the methods we have developed to segment the anatomy, localize the contacts, and provide programming guidance have been integrated into an interactive software package that has been deployed to the clinic and is in routine use at our institution. Without further optimization of our current implementation of the cGANs, speed of execution for the 3D version is 1.5 s when it is 60 s for the 2D version, which is important for the integration of our methods into the clinical workflow. Overall, the study we have conducted shows that cGANS are an effective way to eliminate metallic artifacts in CT images and that the 3D version of the method should be preferred over the 2D version.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

[1] National Institute on Deafness and Other Communication Disorders, 2011, NIDCD Fact Sheet: Cochlear Implants, NIH Publication No. 11-4798. National Institutes of Health, Bethesda, Md., USA.

[2] L. Gjesteby, B. De Man, Y. Jin, H. Paganetti, J. Verburg, D. Giantsoudi, and G. Wang, Metal artifact reduction in CT: where are we after four decades? IEEE Access, 4 (2016), pp. 5826-5849. doi: 10.1109/Access.2016.2608621.

[3] L. Gjesteby, Q. Yang, Y. Xi, B. Claus, Y. Jin, B. De Man, and G. Wang, Reducing metal streak artifacts in CT images via deep learning: pilot results. 14th Int. Meet. Fully Three-Dimensional Image Reconstr. Radiol. Nucl. Med., 14 (6) (2017), pp. 611-614. doi: 10.12059/Fully3D.2017-11-3202009.

[4] I. J. Goodfellow, J. Pouget-Abadie, M. Mirza, B. Xu, D. Warde-Farley, S. Ozair, A. Courville, and Y. Bengio, Generative adversarial nets. In NIPS 2014. URL: http://papers.nips.cc/paper/5423-generative-adversarial-nets.pdf.

[5] K. He, X. Zhang, S. Ren, and J. Sun, Deep residual learning for image recognition. In CVPR 2016. doi: 10.1109/CVPR.2016.90.

[6] S. Holm, A simple sequentially rejective multiple test procedure. Scandinavian Journal of Statistics. 6 (2) (1979), pp. 65-70. doi: 10.2307/4615733.

[7] P. Isola, J. Zhu, T. Zhou, and A. A. Efros, Image-to-image translation with conditional adversarial networks. In CVPR 2017. doi: arXiv:1611.07004.

[8] D. P. Kingma and J. Ba, Adam: a method for stochastic optimization. In ICLR 2015. doi: arXiv:1412.6980.

[9] F. Maes, A. Collignon, D. Vandermeulen, G. Marchal, and P. Suetens, Multimodality image registration by maximization of mutual information. IEEE Trans. Med. Imaging, 16 (2) (1997), pp. 187-198. doi: 10.1109/42.563664.

[10] J. H. McDonald. 2014. Handbook of Biological Statistics (3rd ed.). Sparky House Publishing, Baltimore, Md.

[11] M. Mirza and S. Osindero, Conditional generative adversarial nets. arXiv:1411.1784 [cs, stat], 2014. doi: arXiv:1411.1784.

[12] J. H. Noble, R. F. Labadie, O. Majdani, and B. M. Dawant, Automatic segmentation of intracochlear anatomy in conventional CT. IEEE Trans. Biomed. Eng., 58 (9) (2011), pp. 2625-2632. doi: 10.1109/TBME.2011.2160262.

[13] J. H. Noble, R. F. Labadie, R. H. Gifford, and B. M. Dawant, Image-guidance enables new methods for customizing cochlear implant stimulation strategies. IEEE Trans. Neural Syst. Rehabil. Eng., 21 (5) (2013), pp. 820-829. doi: 10.1109/TNSRE.2013.2253333.

[14] H. S. Park, S. M. Lee, H. P. Kim, and J. K. Seo, Machine-learning-based nonlinear decomposition of CT images for metal artifact reduction. arXiv:1708.00244 [physics.med-ph], 2017. doi: arXiv:1708.00244.

[15] F. A. Reda, T. R. McRackan, R. F. Labadie, B. M. Dawant, and J. H. Noble, Automatic segmentation of intra-cochlear anatomy in post-implantation CT of unilateral cochlear Implant recipients. Med. Image Anal., 18 (3) (2014), pp. 605-615. doi: 10.1016/j.media.2014.02.001.

[16] F. A. Reda, J. H. Noble, R. F. Labadie, and B. M. Dawant, An artifact-robust, shape library-based algorithm for automatic segmentation of inner ear anatomy in post-cochlear-implantation CT. SPIE Proceedings Vol 9034, Medical Imaging 2014: Image Processing; 90342V (2014). doi: 10.1117/12.2043260.

[17] Z. Wang, A. C. Bovik, H. R. Sheikh, and E. P. Simoncelli, Image quality assessment: from error visibility to structural similarity. IEEE Trans. Image Process., 13 (4) (2004), pp. 600-612. doi: 10.1109/TIP.2003.819861.

[18] W. M. Wells III, P. Viola, H. Atsumi, S. Nakajima, and Ron Kikinis, Multi-modal volume registration by maximization of mutual information. Med. Image Anal., 1 (1) (1996), pp. 35-51. URL: https://doi.org/10.1016/S1361-8415(01)80004-9.

[19] X. Yi, E. Walia, and P. Babyn, Generative adversarial network in medical imaging: a review. arXiv:1809.07294 [cs.CV], 2018. doi: arXiv:1809.07294.

[20] Y. Zhang and H. Yu, Convolutional neural network based metal artifact reduction in x-ray computed tomography. IEEE Trans. Med. Imaging, 37 (6) (2018), pp. 1370-1381. doi: 10.1109/TMI.2018.2823083.

[21] Y. Zhao, B. M. Dawant, R. F. Labadie, and J. H. Noble, Automatic localization of closely-spaced cochlear implant electrode arrays in clinical CTs. Med. Phys., 45 (11) (2018), pp. 5030-5040. doi:10.1002/mp.13185.

[22] Y. Zhao, S. Chakravorti, R. F. Labadie, B. M. Dawant, and J. H. Noble, Automatic graph-based method for localization of cochlear implant electrode arrays in clinical CT with sub-voxel accuracy. Med. Image Anal., 52 (2019), pp 1-12. doi: 10.1016/j.media.2018.11.005.

[23] J. Zhu, T. Park, P. Isola, and A. A. Efros, Unpaired image-to-image translation using cycle-consistent adversarial networks. In ICCV 2017. doi: arXiv:1703.10593.

[24] Reda, F. A. et al.: Automatic segmentation of intracochlear anatomy in post-implantation CT. Proc. SPIE 8671, Medical Imaging 2013: Image-Guided Procedures, Robotic Interventions, and Modeling, 867101 (2013).

[25] Ronneberger, O., Fischer, P., and Brox, T.: U-Net: convolutional networks for biomedical image segmentation. arXiv:1505.04597, (2015).

[26] Johnson, J., Alahi, A., and Fei-Fei. L.: Perceptual losses for real-time style transfer and super-resolution. Lect. Notes Comput. Sci. (including Subser. Lect. Notes Artif. Intell. Lect. Notes Bioinformatics) 9906 LNCS, 694-711 (2016).

[27] Li, C. and Wand, M.: Precomputed real-time texture synthesis with markovian generative adversarial networks. Lect. Notes Comput. Sci. (including Subser. Lect. Notes Artif. Intell. Lect. Notes Bioinformatics) 9907 LNCS, 702-716 (2016.)

[28] Ledig, C. et al.: Photo-realistic single image super-resolution using a generative adversarial network. arXiv: 1609.04802, (2017).

What is claimed is:

1. A deep-learning-based method for metal artifact reduction in a computed tomography (CT) image post-operatively acquired with an implant user in a region of interest in which an implant is implanted, comprising:

providing a dataset and a conditional generative adversarial network (cGAN), wherein the dataset comprises a plurality of CT image pairs, randomly partitioned into a training set, a validation set, and a testing set, wherein each CT image pair has a pre-implantation CT (Pre-CT) image and a post-implantation CT (Post-CT) image respectively acquired in the region of interest of a respective implant recipient before and after an implant is implanted in the region of interest, wherein the Pre-CT image and the Post-CT image of each CT image pair are an artifact-free CT image and an artifact-affected CT image, respectively, wherein the cGAN is conditioned on the Post-CT images, comprises a generator and a discriminator that operably compete with each other, and is characterized with a training objective that is a sum of an adversarial loss and a reconstruction loss;

training the cGAN with the plurality of CT image pairs, so that the cGAN learns a mapping from the artifact-affected CT images to the artifact-free CT images;

inputting the post-operatively acquired CT image to the trained cGAN; and generating an artifact-corrected image from the post-operatively acquired CT image by the trained cGAN, wherein metal artifacts are removed in the artifact-corrected image.

2. The method of claim 1, further comprising localizing anatomy structures of interest in the implanted region in the post-operatively acquired CT image by using the artifact-corrected image.

3. The method of claim 1, wherein said providing the dataset comprises registering the Pre-CT images to the Post-CT images using an intensity-based affine registration.

4. The method of claim 1, wherein said providing the dataset comprises cropping 3D patch pairs containing the structures of interest from the Pre-CT and Post-CT image pairs, so that paired patches contain the same structures of interest, one patch with the implant and the other without the implant.

5. The method of claim 1, wherein the cGAN is a three dimensional (3D) network, wherein the generator operably outputs a 1-channel 3D synthetic Pre-CT image responsive to an input of a 1-channel 3D Post-CT image.

6. The method of claim 5, wherein the generator comprises a network including a first number of convolutional blocks followed by a plurality of ResNet blocks, and a second number of convolutional blocks.

7. The method of claim 5, wherein the discriminator is a fully convolutional network that maps an input that is a concatenation of a Post-CT image and the corresponding Pre-CT image, or a Post-CT image and the synthetic Pre-CT image, to a 3D array, to output a scalar obtained by averaging the 3D array.

8. The method of claim 1, wherein the generator, G, is configured to produce an artifact-free image G (x) from a Post-CT image x, wherein the artifact-free image G (x) is not be distinguishable from the real artifact-free Pre-CT image y by the discriminator, D, which is trained further to detect whether the produced artifact-free image G (x) is faked or not, wherein an output of the discriminator D is a probability of an image to be generated by the generator G rather than a true Pre-CT image.

9. The method of claim 1, wherein the training objective of the discriminator D is to assign a high value to the produced artifact-free image G (x) and a low value to the real artifact-free Pre-CT image y, while the training objective of the generator G is to fool the discriminator D to assign a low value to the produced artifact-free image G (x) and a high value to the real artifact-free Pre-CT image y.

10. The method of claim 1, wherein the training objective of the cGAN is characterized with a total loss, L, that is a sum of the adversarial loss, $L_{cGAN}$ (G, D), and the reconstruction loss, $L_{WL_1}$(G), of the cGANs, wherein $$L = \arg\min_G \max_D L_{cGAN}(G, D) + \alpha L_{WL_1}(G),$$

$$L_{cGAN}(G, D) = \min_G \max_D \mathbb{E}_{x,y}[\log(D(x, y))] + \mathbb{E}_x[\log(1 - D(x, G(x)))],$$

$$L_{WL_1}(G) = \mathbb{E}_{x,y}[\|W \circ (y - G(x))\|_1]$$

wherein a is the weight of the WL1 term, and wherein W is the weighting matrix and ○ is the element-wise multiplication operation.

11. The method of claim 10, wherein the weighting matrix W is calculated by creating a bounding box that encloses the structures of interest, wherein the number of voxels inside the bounding box is equal to $N_{in}$ and the number of voxels outside of the bounding box is equal to $N_{out}$; and assigning weights to the voxels inside and outside of the bounding box that are equal to $(N_{in}+N_{out})/N_{in}$ and 1, respectively.

12. The method of claim 1, wherein said training the cGAN comprises training the cGAN alternatively between one stochastic gradient descent step on the discriminator, and one step on the generator, using a minibatch size of 1 and the Adam solver with momentum 0.5.

13. The method of claim 1, wherein said training the cGAN comprises training the cGAN for N epochs in which a fixed learning rate is applied in the first N/2 epochs and a learning rate that is linearly reduced to zero in the second N/2 epochs, wherein N is the number of training epochs and selected so that the cGAN achieves the highest median mean structure similarity (MSSIM).

14. The method of claim 13, wherein N=200, and the fixed learning rate is about 0.0002.

15. The method of claim 1, wherein said training the cGAN comprises applying image augmentation to the training set by rotating each image by a plurality of small random angles in the range of −10 and 10 degrees about the x-axis, y-axis, and z-axis, to create additional training images from each original image.

16. The method of claim 1, wherein the cGAN is a two dimensional (2D) network, wherein the generator operably outputs 2D synthetic artifact-free image responsive to an input of a 2D slice in a volume in which the artifacts are present, wherein once all 2D slices are input, the produced 2D syntheticimages are stacked to each other so as to generate a 3D synthetic Pre-CT image images.

17. The method of claim 16, wherein input images are 2D 3-channel images, each of those is a slice of the 3D 3-channel Post-CT patch, and the target images of the cGAN are 2D 3-channel images in which each channel is identical and is the patch's slice in the Pre-CT that matches the patch's slice in the Post-CT used as input.

18. The method of claim 16, wherein a band-wise intensity normalization (BWN) is applied to the Post-CT patches that acts as a piecewise linear stretch, wherein a 2% percentile ($P_2$), a 98% percentile ($P_{98}$) and a 99.95% percentile ($p_{99.95}$) of the intensity values of each Post-CT patch are calculated, and the patch is separated into three channels, and wherein the whole patch is coped into channels 1, 2, and 3, the intensity values in channels 1, 2, and 3 are clamped to the ranges $P_2$ to $(P_2+p_{98})/2$, $(P_2+p_{98})/2$ to $P_{98}$, and $P_{98}$ to $p_{99.95}$, respectively, and each channel is normalized to the −1 to 1 range.

19. The method of claim 18, wherein for each Pre-CT patch, the intensity values are clamped to the range between the bottom 1% and the top 1% voxel values, and the Pre-CT patch is normalized to the −1 to 1 range.

20. The method of claim 1, wherein the region of interest is a region in which an implant is implanted, wherein the region of interest includes ear, brain, heart, or other organs of a living subject.

21. The method of claim 20, wherein the structures of interest comprise anatomical structures in the region of interest.

22. The method of claim 21, wherein the anatomical structures comprise intra cochlear anatomy (ICA).

23. The method of claim 20, wherein the implant is a cochlear implant, a deep brain stimulator, or a pacemaker.

24. A non-transitory tangible computer-readable medium storing instructions which, when executed by one or more processors, cause a system to perform the method of claim 1.

* * * * *